(12) United States Patent
Kim et al.

(10) Patent No.: US 10,322,999 B2
(45) Date of Patent: Jun. 18, 2019

(54) OXINDOLES DERIVATIVES, PREPARATION METHOD THEREOF AND PHARMACEUTICAL COMPOSITIONS FOR THE PREVENTION OR TREATMENT OF CANCER CONTAINING THE SAME AS AN ACTIVE INGREDIENT

(71) Applicant: RESEARCH & BUSINESS FOUNDATION SUNGKYUNKWAN UNIVERSITY, Suwon-si, Gyeonggi-do (KR)

(72) Inventors: In Su Kim, Suwon-si (KR); Hyung Sik Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/988,781

(22) Filed: May 24, 2018

(65) Prior Publication Data
US 2018/0339965 A1    Nov. 29, 2018

(30) Foreign Application Priority Data
May 26, 2017   (KR) .......................... 10-2017-0065385

(51) Int. Cl.
*A61P 35/00* (2006.01)
*C07D 209/34* (2006.01)

(52) U.S. Cl.
CPC ............ *C07D 209/34* (2013.01); *A61P 35/00* (2018.01)

(58) Field of Classification Search
CPC .............................. C07D 209/34; A61P 35/00
See application file for complete search history.

(56) References Cited

PUBLICATIONS

Han et al. "One-pot Synthesis of Oxindoles through C—H Alkylation and Intramolecular Cyclization of Azobenzenes with Internal Olefins" Advanced Synthesis and Catalysis, Published Apr. 2, 2017, vol. 359, No. 14, pp. 2396-2401.*

* cited by examiner

*Primary Examiner* — Joseph R Kosack
(74) *Attorney, Agent, or Firm* — NSIP Law

(57) ABSTRACT

The present invention relates to a novel oxindole derivative having anticancer activity, a preparation method thereof, and a method for treating cancer using the same. More specifically, the present invention relates to an oxindole derivative produced as a result of CH alkylation and subsequent intramolecular cyclization reaction using a rhodium (III) catalyst, a preparation method of the same, and a method for treating cancer containing the same as an active ingredient. The novel oxindole derivatives according to the present invention have excellent anticancer activity against various human cancer cell lines and are expected to be useful for the treatment of cancer. In addition, the preparation method of an oxindole derivative using the rhodium (III) catalyst of the present invention can be applied and introduced into a wide range of functional groups, and is a reaction having positional selectivity and chemical selectivity. As a reaction for synthesizing a new drug or a compound having biological activity, it will be useful.

13 Claims, 6 Drawing Sheets

OXINDOLES DERIVATIVES, PREPARATION METHOD THEREOF AND PHARMACEUTICAL COMPOSITIONS FOR THE PREVENTION OR TREATMENT OF CANCER CONTAINING THE SAME AS AN ACTIVE INGREDIENT

STATEMENT REGARDING GOVERNMENT RIGHTS

The present invention was undertaken with the support of "Late-stage Drug Optimization Laboratory" No. 2016R1A4A1011189 grant funded by the National Research Foundation of Korea (NRF) grant funded by the Korea Government (MSIP).

CROSS-REFERENCE TO RELATED APPLICATIONS

This application claims priority based on Korean Patent Application No. 10-2017-0065385, filed on May 26, 2017, the contents of which is incorporated herein by reference in its entirety.

FIELD OF THE INVENTION

The present invention relates to a novel oxindole derivative having an anticancer activity, preparation method thereof, and a method for treating a disease containing the same as an active ingredient.

BACKGROUND OF THE INVENTION

The oxindole skeleton has been recognized as a hetero ring structure commonly found in synthetic compounds in physiologically active natural products and medical applications. In particular, 3-substituted and spirooxindole derivatives have been implicated in a variety of biological activities including serotonin, anti-tumor, anti-alzheimer's, anti-parkinsonian, glycoprotein mediated MDR inhibition, antibacterial and anti-inflammatory activity. The oxindole also acts as a precursor for the synthesis of other heterocyclic compounds, including indoles and isatins. Therefore, the development of a highly efficient new strategy for the synthesis of oxindole structures in organic synthesis has received much attention. With the recent development of direct catalytic C—H functionalization, many studies have been carried out on the synthesis of oxindole via oxidative C—H functionalization without a transition metal catalyst or metal.

In particular, tandem cyclization of acrylamides has attracted attention in the synthesis of various functionalized oxindoles. Another route is the synthesis by Ir or Cu catalyst intramolecular cyclization of β-ketoamide derivatives. In addition, the aromatic C—H functionalization of α-diazoamides by Ag or Rh catalysis is another effective method for synthesizing C3-functionalized oxindoles. However, these processes require essentially starting materials with certain functional groups, which also form subclasses of oxindole.

Recently, azobenzene has been used for catalytic C—H functionalization by using an azo functional group as an aromatic group. In this context, C—H addition and subsequent cyclization reactions are applied for the purpose of constructing various N-heterocyclic molecules.

For example, the synthesis of (2H)-indazoles through catalytic redox neutral coupling of Rh (III), Co (III) or Re (0) with azobenzene and aryl aldehydes is known. In addition, the formation of (2H)-indazole was initiated by Pd (II) catalyzed oxidative acylation and aldehyde reduction cyclization of azobenzene. The cyclization capture approach by Rh (III) catalysts, which synthesize a variety of 1-aminoindoles, is also known.

Also, the synthesis of benzotriazoles in azobenzene and organic azides is also known through amination and cyclization of Rh (III) or Pd (II) catalysis. Recently, the present inventors have demonstrated highly substituted cyanolins derived from azobenzene and α-diazo esters under Rh (III) catalyst (S. Sharma, S H Han, S. Han, W. Ji. J. Oh, S.-Y. Lee, J S Oh, Y H Jung, I S Kim, Org. Lett., 2015, 17, 2852). Other heterocycles, such as cinnoline, 3-acyl-indazole and indole, were also formed by C—H functionalization and cyclization strategies.

SUMMARY OF THE INVENTION

Technical Problems to Solve

The present invention has been made to solve the above-mentioned problems in the prior art, the inventors of the present invention have confirmed the prevention or therapeutic effect of cancer through inhibition of cancer cell proliferation by preparing a novel oxindole derivative having anticancer activity and treating it, on the basis of this, the present invention has been completed.

Accordingly, an object of the present invention is to provide a novel oxindole derivative having an anticancer activity and a pharmaceutically acceptable salt thereof.

Also, another object of the present invention is to provide a preparation method of a novel oxindole derivative having an anticancer activity.

Still another object of the present invention is to provide a method for treating cancer, which comprises administering a novel oxindole derivative having an anticancer activity, an isomer thereof, or a pharmaceutically acceptable salt thereof to a cancer patient for treatment of cancer.

However, technical problems to be solved in the present invention are not limited to the above-described problems, and other problems which are not described herein will be fully understood by those of ordinary skill in the art from the following descriptions.

Technical Solutions

In order to achieve the above-described objects of the present invention, the present invention provides an oxindole derivative represented by following Formula 1, an isomer thereof, or a pharmaceutically acceptable salt thereof:

[Formula 1]

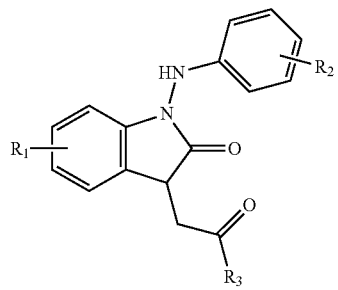

in the Formula 1, wherein $R_1$ and $R_2$ are one or more substituents and are independently hydrogen, halogen, or C1-C6 alkyl, and each of $R_1$ and $R_2$ is a substituent at least at an ortho, meta or para position;

wherein $R_3$ is NHMe, NHEt, NHBn, NHCyHex, NH$^t$Bu, NH$_2$, NHPh, NHCH$_2$Ph, NHCO$_2$Me, NHCO$_2$Et, NHCHCH$_3$CO$_2$Me, OMe, O$^n$Bu, O$^i$Pr, or O$^i$Bu;

wherein Me is CH$_3$, Et is CH$_2$CH$_3$, Bn is CH$_2$Ph (benzyl), Cyhex is cyclohexyl, $^t$Bu is tertiarybutyl, $^n$Bu is normalbutyl. $^i$Pr is iso Isopropyl. and $^i$Bu is isobutyl.

Further, the present invention provides a preparation method of an oxindole derivative represented by following Formula 1, comprising a step (S1) of performing a C—H alkylation reaction in the presence of a rhodium catalyst by mixing a compound represented by following Formula 2, a compound represented by following Formula 3 or 4, and an additive, and a step (S2) of performing an intramolecular cyclization reaction by adding a zinc powder and an additive after the C—H alkylation reaction:

[Formula 2]

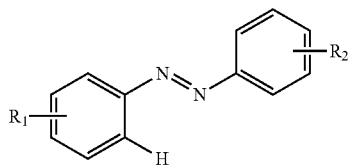

in the Formula 2, wherein $R_1$ and $R_2$ are one or more substituents and are independently hydrogen, halogen, or C1-C6 alkyl, and each of $R_1$ and $R_2$ is a substituent at least at an ortho, meta or para position;

[Formula 3]

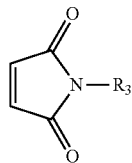

[Formula 4]

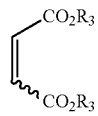

in the Formulas 3 to 4, wherein $R_3$ is NHMe, NHEt, NHBn, NHCyHex, NH$^t$Bu, NH$_2$, NHPh, NHCH$_2$Ph, NHCO$_2$Me, NHCO$_2$Et, NHCHCH$_3$CO$_2$Me, OMe, O$^n$Bu, O$^i$Pr, or O$^i$Bu.

Wherein Me is CH$_3$, Et is CH$_2$CH$_3$, Bn is CH$_2$Ph (benzyl), Cyhex is cyclohexyl, $^t$Bu is tertiarybutyl, $^n$Bu is normalbutyl, $^i$Pr is iso Isopropyl, and $^i$Bu is isobutyl.

As another exemplary embodiment of the present invention, the rhodium catalyst may be a cyclopentadienyl rhodium (III) complex catalyst substituted or unsubstituted with a C1-C5 alkyl, more preferably pentamethylcyclopentadienylrhodium (III) chloride dimer ([RhCp*Cl$_2$]$_2$) catalyst.

In another embodiment of the present invention, the step (S1) may be performed in a dichloroethene (DCE) solvent.

In another embodiment of the present invention, the step (S2) may be performed in a solvent of ethanol, methanol or a mixture thereof.

As still another exemplary embodiment of the present invention, the additive in step (S2) may be an acid additive, more preferably the acid additive in step (S2) may be acetic acid, ammonium chloride (NH$_4$Cl) or a mixture thereof, but is not limited thereto.

As yet another exemplary embodiment of the present invention, the additive in the step (S1) may be an acid additive, more preferably the acid additive in step (S1) may be pivalic acid, acetic acid, or a mixture thereof, but is not limited thereto.

Further, the present invention provides a pharmaceutical composition for preventing or treating cancer, comprising an oxindole derivative, an isomer thereof, or a pharmaceutically acceptable salt thereof represented by the Formula 1 as an active ingredient.

In addition, the present invention provides a method for treating cancer, which comprises administering an oxindole derivative, an isomer thereof, or a pharmaceutically acceptable salt thereof represented by the Formula 1 to a cancer patient for treatment of cancer.

As an exemplary embodiment of the present invention, the cancer may be at least one selected from the group consisting of prostate cancer, breast cancer, ovarian cancer, lung cancer, and kidney cancer.

Furthermore, the present invention provides a method for preventing or treating cancer, comprising the step of administering the pharmaceutical composition to a subject.

Further, the present invention provides the use of the pharmaceutical composition for preventing or treating cancer.

Advantageous Effects

The novel oxindole derivatives according to the present invention exhibit excellent anticancer activity against various human cancer cells, and are expected to be useful as pharmaceutical compositions for prevention and treatment of cancer.

Also, the method according to the invention is characterized in that the oxindole is synthesized by a single step through positional CH alkylation of azobenzene and internal olefins (maleimide, maleate and fumarate) with a rhodium (III) catalyst and subsequent reductive intramolecular cyclization in the presence of a rhodium catalyst, which is obtained by ortho-alkylated azobenzene through a rhodium catalyst in the presence of an acetic acid additive in a dichloroethane solvent, and then form a C3-functionalized oxindole using zinc powder and acetic acid. This is advantageous in that the efficiency and yield of the process can be greatly increased since the production of oxindole can be synthesized by a single process as compared with the conventional production of oxindole, which has to proceed in multiple steps.

In addition, the oxindole skeleton is expected to be very useful in the synthesis of new medicines or compounds having biological activity.

BRIEF DESCRIPTIONS OF THE DRAWINGS

DETAILED DESCRIPTION OF THE INVENTION

Figure 1:
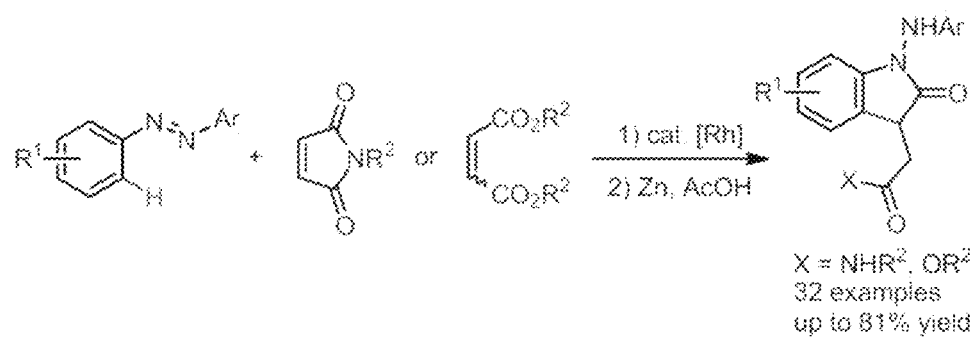
FIG. 1 shows a preparation method of an oxindole derivative of the present invention.
Figure 2:
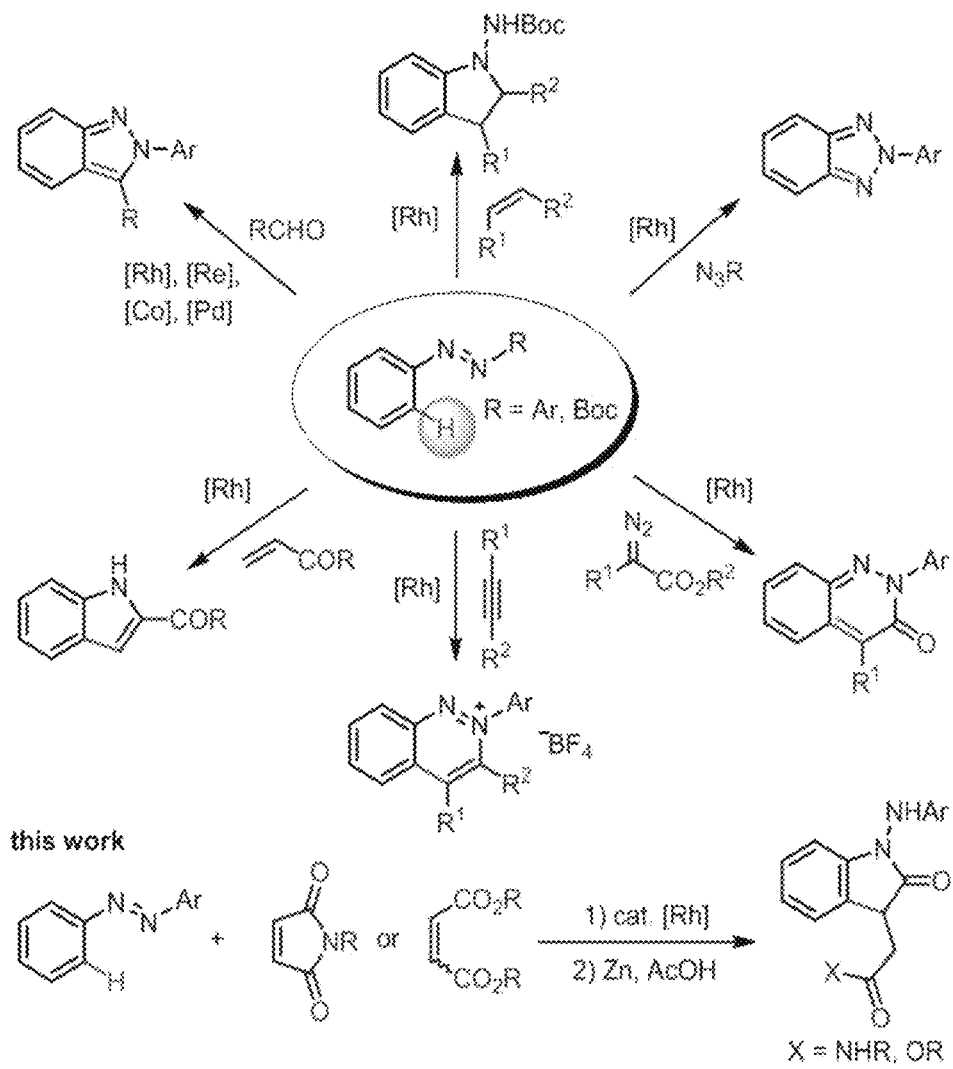
FIG. 2 shows a preparation method of an oxindole derivative using the rhodium (III) catalyst of the present invention (this work) and a conventional preparation method of an oxindole derivative (previous work).

The present invention provides a novel oxindole derivative having an anticancer activity, an isomer thereof, a pharmaceutically acceptable salt thereof, and a composition for preventing or treating cancer containing the same as an active ingredient. In addition, the compound according to the present invention inhibits the proliferation of cancer cells and has a prophylactic or therapeutic effect against cancer, and thus can be usefully used for prevention or treatment of cancer. Accordingly, the present invention provides a method for treating cancer, which comprises administering an oxindole derivative represented by following Formula 1, an isomer thereof, or a pharmaceutically acceptable salt thereof to a cancer patient for treatment of cancer.

Hereinafter, the present invention will be described in detail.

The present invention provides an oxindole derivative represented by following Formula 1, an isomer thereof, or a pharmaceutically acceptable salt thereof:

[Formula 1]

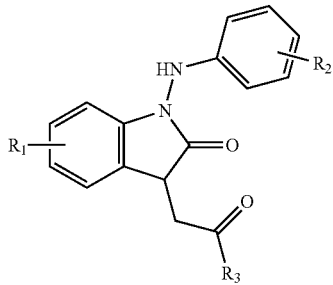

in the Formula 1, wherein $R_1$ and $R_2$ are one or more substituents and are hydrogen, halogen, or C1-C6 alkyl, and each of $R_1$ and $R_2$ is a substituent at least at an ortho, meta or para position;

wherein $R_3$ is NHMe, NHEt, NHBn, NHCyHex, NH$^t$Bu, NH$_2$, NHPh, NHCH$_2$Ph, NHCO$_2$Me, NHCO$_2$Et. NHCHCH$_3$CO$_2$Me, OMe, O$^n$Bu, O$^i$Pr. or O$^i$Bu;

wherein Me is CH$_3$. Et is CH$_2$CH$_3$, Bn is CH$_2$Ph (benzyl). Cyhex is cyclohexyl, $^t$Bu is tertiarybutyl, $^n$Bu is normalbutyl, $^i$Pr is iso Isopropyl, and $^i$Bu is isobutyl.

More preferably, in the Formula 1, Wherein $R_1$ and $R_2$ may be independently hydrogen, methyl, ethyl, fluoro, chloro or bromo, and $R_1$ and $R_2$ are one or more substituents and each of $R_1$ and $R_2$ is a substituent at least at an ortho, meta or para position;

The following describes the definitions of various substituents for preparing the compounds according to the invention.

The term "C1-C6 alkyl" as used herein means a monovalent alkyl group of 1 to 6 carbon atoms. The term is exemplified by functional groups such as methyl, ethyl, n-propyl, i-propyl, n-butyl, i-butyl, tert-butyl, n-hexyl and the like.

The alkyls described in the present invention, as well as the substituents comprising the other alkyl moieties, include both linear and branched forms.

Preferred embodiments of the oxindole derivative represented by the Formula 1 according to the present invention are as follows:

2-(7-Ethyl-1-((2-ethylphenyl)amino)-2-oxoindolin-3-yl)-N-methylacetamide (3a);

N-methyl-2-(7-methyl-2-oxo-1-aq(o-tolylamino)indolin-3-yl)acetamide (3b);

2-(1-((2,3-dimethylphenyl)amino)-6,7-dimethyl-2-oxoindolin-3-yl)-N-methylacetamide (3c);

2-(6-fluoro-1-((3-fluoro-2-methylphenyl)amino)-7-methyl-2-oxoindolin-3-yl)-N-methylacetamide (3d);

2-(6-Chloro-1-((3-chloro-2-methylphenyl)amino)-7-methyl-2-oxoindolin-3-yl)-N-methylacetamide (3e);

2-(6-bromo-1-((3-bromo-2-methylphenyl)amino)-7-methyl-2-oxoindolin-3-yl)-N-methylacetamide (3f);

2-(1-((2,4-dimethylphenyl)amino)-5,7-dimethyl-2-oxoindolin-3-yl)-N-methylacetamide (3g);

2-(5-fluoro-1-((4-fluoro-2-methylphenyl)amino)-7-methyl-2-oxoindolin-3-yl)-N-methylacetamide (3h);

2-(5-chloro-1-((4-chloro-2-methylphenyl)amino)-7-methyl-2-oxoindolin-3-yl)-N-methylacetamide (3i);

2-(1-((2,5-dimethylphenyl)amino)-4,7-dimethyl-2-oxoindolin-3-yl)-N-methylacetamide (3j);

2-(4-fluoro-1-((5-fluoro-2-methylphenyl)amino)-7-methyl-2-oxoindolin-3-yl)-N-methylacetamide (3k);

2-(4-Bromo-1-((5-bromo-2-methylphenyl)amino)-7-methyl-2-oxoindolin-3-yl)-N-methylacetamide (3l);

N-methyl-2-(2-oxo-1-(phenylamino)indolin-3-yl)acetamide (3m);

N-methyl-2-(5-methyl-2-oxo-1-(p-tolylamino)indolin-3-yl) acetamide (3n);

2-(6-ethyl-1-((3-ethylphenyl)amino)-2-oxoindolin-3-yl)-N-methylacetamide (3o);

2-(1-(2,4-Dimethylphenylamino)-7-methyl-2-oxoindolin-3-yl)-N-methylacetamide (3p);

2-(5,7-dimethyl-2-oxo-1-(o-tolylamino)indolin-3-yl)-N-methylacetamide (3p');

N-methyl-2-(2-oxo-1-(p-tolylamino)indolin-3-yl) acetamide (3q);

N-methyl-2-(5-methyl-2-oxo-1-(phenylamino)indolin-3-yl) acetamide (3q');

2-(1-(4-Chloro-2-methylphenylamino)-7-methyl-2-oxoindolin-3-yl)-N-methylacetamide (3r);

2-(5-chloro-7-methyl-2-oxo-1-(o-tolylamino)indolin-3-yl)-N-methylacetamide (3r');

N-Ethyl-2-(7-ethyl-1-((2-ethylphenyl) amino)-2-oxoindolin-3-yl)acetamide (4b);

N-benzyl-2-(7-ethyl-1-((2-ethylphenyl)amino)-2-oxoindolin-3-yl)acetamide (4c);

N-cyclohexyl-2-(7-ethyl-1-((2-ethylphenyl)amino)-2-oxoindolin-3-yl)acetamide (4d);

N-(tert-butyl)-2-(7-ethyl-1-((2-ethylphenyl)amino)-2-oxoindolin-3-yl)acetamide (4e);

2-(7-Ethyl-1-((2-ethylphenyl)amino)-2-oxoindolin-3-yl)ac-
etamide (4t);
2-(7-Ethyl-1-((2-ethylphenyl)amino)-2-oxoindolin-3-yl)-N-
phenylacetamide (4g);
Ethyl(2-(7-ethyl-1-((2-ethylphenyl)amino)-2-oxoindolin-3-
yl)acetyl) carbamate (4h);
Methyl(2-(7-ethyl-1-((2-ethylphenyl)amino)-2-oxoindolin-
3-yl)acetyl)carbamate (4i);
Methyl(2-(7-ethyl-1-((2-ethylphenyl)amino)-2-oxoindolin-
3-yl)acetyl)-L-alaninate (4j);
Methyl 2-(7-ethyl-1-((2-ethylphenyl)amino)-2-oxoindolin-
3-yl)acetate (6a);
Butyl 2-(7-ethyl-1-((2-ethylphenyl) amino)-2-oxoindolin-3-
yl)acetate (6b);
Isopropyl 2-(7-ethyl-1-((2-ethylphenyl)amino)-2-oxoindo-
lin-3-yl)acetate (6c); and
Isobutyl 2-(7-ethyl-1-((2-ethylphenyl)amino)-2-oxoindolin-
3-yl)acetate (6d).

The compound of the present invention can be used in the form of a pharmaceutically acceptable salt. As the salt, acid addition salt formed by a pharmaceutically acceptable free acid is useful.

The term "salt" as used herein is useful as acid addition salt formed by a pharmaceutically acceptable free acid. Acid addition salts are obtained from inorganic acids such as hydrochloric acid, nitric acid, phosphoric acid, sulfuric acid, hydrobromic acid, hydroiodic acid, nitrous acid or phosphorous acid and non-toxic organic acids such as aliphatic mono and dicarboxylates, phenyl-substituted alkanoates, hydroxyalkanoates and alkanedioate, aromatic acid, or aliphatic and aromatic sulfonic acids. Such pharmaceutically non-toxic salts include sulfate, pyrosulfate, bisulfate, sulfite, bisulfite, nitrate, phosphate, monohydrogenphosphate, dihydrogenphosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suverate, sebacate, fumarate, malate, butene-1,4-dioate, hexane-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, β-hydroxybutyrate, glycolate, maleate, tartrate, methanesulfonate, propanesulfonate, naphthalene-1-sulfonate, naphthalene-2-sulfonate or mandelate.

The acid addition salt according to the present invention can be prepared by a conventional method, for example, by dissolving the compound in an excess amount of an aqueous acid solution and precipitating the salt using a water-miscible organic solvent such as methanol, ethanol, acetone or acetonitrile. It is also possible to prepare an acid addition salt by evaporating a solvent or excess acid in this mixture and then drying or by suction filtration of the precipitated salt.

In addition, bases may be used to make pharmaceutically acceptable metal salts. The alkali metal or alkaline earth metal salt is obtained, for example, by dissolving the compound in an excess of an alkali metal hydroxide or alkaline earth metal hydroxide solution, filtering the insoluble compound salt, and evaporating and drying the filtrate. It is preferable for the metal salt to produce sodium, potassium or calcium salt. The corresponding silver salt is obtained by reacting an alkali metal or alkaline earth metal salt with a suitable silver salt (such as silver nitrate).

In addition, the compounds of the present invention include not only pharmaceutically acceptable salts, but also all salts, isomers, hydrates and solvates which can be prepared by conventional methods.

According to another aspect of the present invention, the present invention provides a preparation method of an oxindole derivative represented by following Formula 1, comprising a step (S1) of performing a C—H alkylation reaction in the presence of a rhodium catalyst by mixing a compound represented by following Formula 2, a compound represented by following Formula 3 or 4, and an additive; and a step (S2) of performing an intramolecular cyclization reaction by adding a zinc powder and an additive after the C—H alkylation reaction. Wherein process is shown in FIG. 1.

[Formula 2]

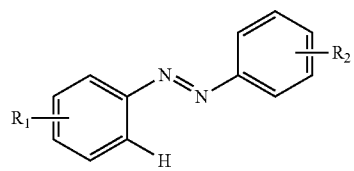

[Formula 3]

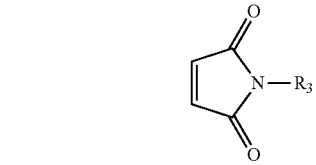

[Formula 4]

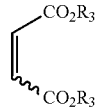

In the Formulas 2 to 4, $R_1$, $R_2$ and $R_3$ are the same as defined in the Formula 1.

The preparation method of an oxindole derivative of the present invention is a process for synthesizing oxindole by a single step through CH alkylation and reductive intramolecular cyclization in the presence of a rhodium catalyst, which the C3 functionalized oxindole was first synthesized using zinc powder and acetic acid after ortho-alkylation of azobenzene through a rhodium catalyst.

The rhodium catalyst of the present invention may be cyclopentadienyl rhodium (III) complex catalyst substituted or unsubstituted with C1-C5 alkyl, more preferably, it may be a pentamethylcyclopentadienylrhodium (III) chloride dimer([RhCp*Cl$_2$]$_2$) and can be used in an amount of 1 to 4 mol % Preferably 2 to 3 mol % based on 1 mol of the compound of the formula 2.

The additive in the step (S2) is preferably an acid additive, and the acid additive is more preferably at least one selected from the group consisting of acetic acid, ammonium chloride (NH$_4$Cl) and a mixture thereof in terms of yield, but is not limited thereto.

The additive in the step (S1) is preferably an acid additive, and the acid additive is more preferably at least one selected from the group consisting of pivalic acid (PiOH) and acetic acid in terms of yield, but is not limited thereto.

The reaction according to an embodiment of the present invention can be carried out in an organic solvent, and it is not necessary to limit the organic solvent as long as it can dissolve the reactant.

Examples of the organic solvent may be selected from the group consisting of dichloroethene (DCE), ethanol, methanol, toluene, and mixtures thereof, but is not limited thereto.

In view of the reaction efficiency, solubility of the reactants, and ease of removal, the step (S1) may be performed in a solvent of Dichloroethene (DCE), but is not limited thereto.

In view of the reaction efficiency, solubility of the reactants, and ease of removal, the step (S2) may be performed in a solvent of ethanol, methanol or a mixture thereof, but is not limited thereto.

As an exemplary embodiment of the present invention, the oxindole derivative represented by the Formula 1 was prepared, and the structure was analyzed and confirmed by NMR or Mass spectroscopy (see Examples 1 to 8).

In another aspect of the present invention, the present invention provides a pharmaceutical composition for preventing, ameliorating or treating cancer comprising an oxindole derivative represented by the Formula 1, an isomer thereof, or a pharmaceutically acceptable salt thereof as an active ingredient.

The present invention provides a method for treating cancer, which comprises administering an oxindole derivative represented by the formula 1, an isomer thereof, or a pharmaceutically acceptable salt thereof to a cancer patient for treatment of cancer.

The term "preventing" as used herein means all the actions that inhibit cancer or delay the onset of cancer by administration of the pharmaceutical composition according to the present invention.

The term "treatment" as used herein means all the actions for improving or alleviating symptoms of cancer by administration of the pharmaceutical composition according to the present invention.

The term "Cancer", a target disease of the present invention, is classified into diseases in which normal tissue cells proliferate unlimitedly for any reason and continue rapid development regardless of the life phenomenon of the living body or the surrounding tissue state, and the cancer in the present invention is preferably may be prostate cancer, breast cancer, ovarian cancer, lung cancer, or kidney cancer, but is not limited to this kind.

As an exemplary embodiment of the present invention, the anticancer activity against various human cancer cells was evaluated using the oxindole derivatives synthesized according to the preparation method of the present invention (see example 9), the compounds of the present invention were found to exhibit strong anticancer activities against various carcinomas.

Accordingly, the oxindole derivative represented by the Formula 1 according to the present invention, an isomer thereof, or a pharmaceutically acceptable salt thereof may be usefully used for preventing, ameliorating or treating cancer containing the same as an active ingredient.

The pharmaceutical composition according to the present invention may contain a pharmaceutically acceptable carrier addition to the active ingredient. In this case, pharmaceutically acceptable carriers include those conventionally used in the Formulation, including lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil, etc, but is not limited thereto. Further, in addition to the above components, a lubricant, a wetting agent, a sweetener, a flavoring agent, an emulsifying agent, a suspending agent, a preservative, and the like may be further included.

The pharmaceutical composition of the present invention may be administered orally or parenterally (for example, intravenously, subcutaneously, intraperitoneally or topically) depending on the intended method, and the dose may be determined depending on the condition and the weight of the patient, the type of administration, the route of administration, and the time, but can be appropriately selected by those skilled in the art.

The oxindole derivative of the present invention, an isomer thereof, or a pharmaceutically acceptable salt thereof is administered in a pharmaceutically effective amount. In the present invention, "pharmaceutically effective amount" means an amount sufficient to treat a disease at a reasonable benefit/risk ratio applicable to medical treatment, and an effective dose level is determined depending on the factors including the kind of disease, severity, the activity of the drug, the sensitivity to the drug, the time of administration, the route of administration, the rate of excretion, the duration of the treatment, and co-administered drugs, and other factors well known in the medical arts. The pharmaceutical composition according to the present invention can be administered as an individual therapeutic agent or in combination with other therapeutic agents, and can be administered sequentially or simultaneously with conventional therapeutic agents, and can be administered singly or in multiple doses. It is important to take all of the above factors into consideration and administer an amount that can achieve the maximum effect in a minimal amount without side effects, which can be easily determined by those skilled in the art.

Specifically, the effective amount of the oxindole derivative of the present invention, an isomer thereof, or a pharmaceutically acceptable salt thereof may be determined depending on the age, sex, condition, body weight, absorbency rate of the active ingredient in the body, inactivation rate and excretion rate, type of disease, and drugs used in combination. Generally, 0.001 to 150 mg, preferably 0.01 to 100 mg, per kg body weight can be administered daily or every other day, or one to three divided doses per day. However, the dosage may be varied depending on the route of administration, the severity of obesity, sex, weight, age, etc. Therefore, the dosage is not limited to the scope of the present invention by any means.

In another aspect of the present invention, the present invention provides a method for treating cancer, which comprises administering the oxindole derivative, an isomer thereof, or a pharmaceutically acceptable salt thereof to a cancer patient. In the present invention, the term "patient" refers to a subject in need of treatment for a disease, and more specifically refers to a mammal such as a human or non-human primate, mouse, dog, cat, horse, cattle and so on.

As shown in FIG. 1, the novel oxindole derivative produced as a result of the reaction using the rhodium (III) catalyst of the present invention showed excellent anticancer activity against various human cancer cells, which is expected to be useful as a pharmaceutical composition for prevention and treatment of cancer. In addition, preparation method of an oxindole derivative using the rhodium (III) catalyst of the present invention can be applied and introduced into a wide range of functional groups. And this is a reaction with positional selectivity and chemical selectivity, which will be very useful in the synthesis of new drugs or compounds with biological activity.

Hereinafter, preferred examples for helping the understanding of the present invention will be suggested. However, the following Examples are provided only to more easily understand the present invention, and the content of the present invention are not limited by the following Examples.

EXAMPLE

In the examples of the present invention, commercially available reagents were used without further purification unless otherwise mentioned. Closed tubes (13×100 mm$^2$) were purchased from fischer scientific, dried in the oven overnight and then cooled to room temperature prior to use. Thin layer chromatography was performed using plates coated with Kieselgel 60 F$_{254}$ (Merck) and in the case of flash column chromatography, E. Merck Kieselgel 60 (230-400 mesh) was used.

Nuclear magnetic resonance spectra (1H and 13C NMR) were recorded using a CDCl$_3$ solution in a bruker unity 400 and 500 spectrometer and chemical shifts were reported in parts per million (ppm). The resonance pattern is represented by s (singlet), d (doublet), t (triplet), q (quartet), quint (quintet), sext (sextet) and m (multiplet). And Br is used to represent a wide signal. The coupling constant (J) is expressed in hertz (Hz).

IR spectra were recorded on a Varian 2000 infrared spectrophotometer and reported as cm$^{-1}$. High resolution mass spectra (HRMS) were analyzed using a JEOL JMS-600 spectrometer.

Example 1

Search for Optimum Reaction Conditions for the Synthesis of Oxindole Derivatives In this Example 1, the coupling conditions of azobenzene (1a) and N-methylmaleimide (2a) were investigated under rhodium catalysts, and optimization conditions were derived as shown in reaction scheme 1 below in order to set optimum reaction conditions for the synthesis of oxindoles derivatives through the coupling reaction of azobenzene and maleimide. As a result, as shown in table 1, the cationic rhodium complex derived from [RhCp*Cl$_2$]$_2$ and AgSbF$_6$ catalyzed the coupling reaction of 1a and 2a, which was confirmed that the ortho-alkyl paraazobenzene (3aa) was produced in a yield of 18% (Item 1). Thereafter, acidic additives such as PivOH and AcOH were treated under different conditions to confirm that 3aa was obtained in high yield (Items 2 and 3). However, it has been found that other additives such as NaOAc, AgOAc, Cu(OAc)$_2$ and Ag$_2$CO$_3$ are less effective in this synthesis, as shown in items 4-7.

As a result of the control experiment, excluding the AgSbF$_6$ or Rh (III) catalyst, it was found that 3aa was not formed (items 8 and 9), and other catalysts ([Ru(p-cymene) Cl$_2$]$_2$ and [CoCp*(CO)I$_2$]) such as Ru (II) and Co (Ill) were not effective in the coupling reaction (Item 10 and Item 11). During screening of a range of solvents, DCE was found to exhibit the highest reactivity towards formation of 3aa (items 12-15). The reaction also yielded 3aa in 90% yield using one equivalent of AcOH (item 16). However, lowering the amount of AcOH and Rh (III) catalysts reduced the formation of 3aa to 81% and 69%, respectively (items 17 and 18).

[Chemical reation Formula 1]

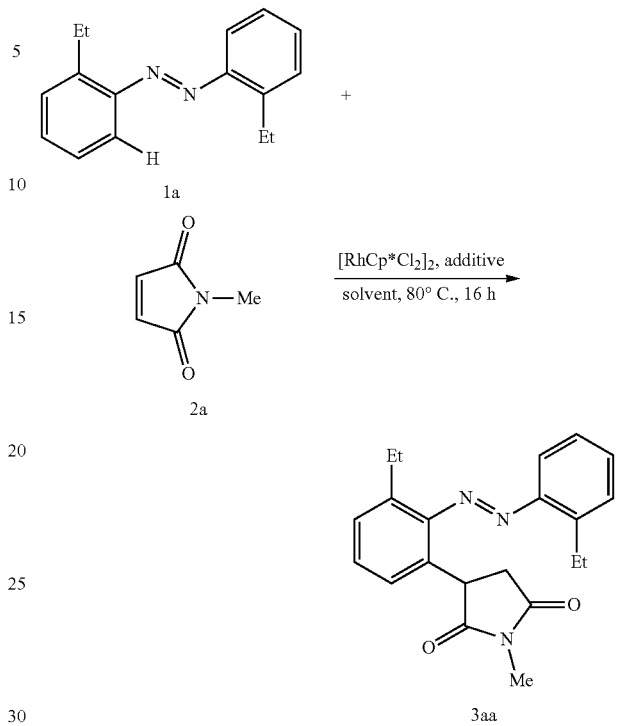

Reaction conditions: 1a (0.2) mmol), 2a (0.3 mmol), [RhCp*Cl$_2$]$_2$ (2.5 mol %), Additive (mol %, listed in the table), solvent (1 mL), reaction in pressure tubes for 16 hours at 80° C.

TABLE 1

| Item | Additive (mol %) | Catalyst | Solvent | Yield[b] |
|---|---|---|---|---|
| 1 | AgSbF$_6$(10) | Rh(III) | DCE | 18 |
| 2 | AgSbF$_6$(10), PivOH(200) | Rh(III) | DCE | 89 |
| 3 | AgSbF$_6$(10), AcOH(200) | Rh(III) | DCE | 88 |
| 4 | AgSbF$_6$(10), NaOAc(200) | Rh(III) | DCE | trace |
| 5 | AgSbF$_6$(10), AgOAc(200) | Rh(III) | DCE | 11 |
| 6 | AgSbF$_6$(10), Cu(OAc)2(200) | Rh(III) | DCE | 75 |
| 7 | AgSbF$_6$(10), Ag2CO3(200) | Rh(III) | DCE | N.R. |
| 8 | AcOH (200) | Rh(III) | DCE | N.R. |
| 9[c] | AgSbF$_6$(10), AcOH(200) | — | DCE | N.R. |
| 10[d] | AgSbF$_6$(10), AcOH(200) | Ru(II) | DCE | 10 |
| 11[e] | AgSbF$_6$(10), AcOH(200) | Co(III) | DCE | 20 |
| 12 | AgSbF$_6$(10), AcOH(200) | Rh(III) | THF | 39 |
| 13 | AgSbF$_6$(10), AcOH(200) | Rh(III) | MeCN | N.R. |
| 14 | AgSbF$_6$(10), AcOH(200) | Rh(III) | t-BuOH | N.R. |
| 15 | AgSbF$_6$(10), AcOH(200) | Rh(III) | DMSO | N.R. |
| 16 | AgSbF$_6$(10), AcOH(100) | Rh(III) | DCE | 90 |
| 17 | AgSbF$_6$(10), AcOH(50) | Rh(III) | DCE | 81 |
| 18[f] | AgSbF$_6$(5), AcOH(200) | Rh(III) | DCE | 69 |

(*[c]was reacted without addition of [RhCp*Cl$_2$]$_2$, [d]added [Ru(p-cymene)Cl$_2$]$_2$ (2.5 mol %) instead of [RhCp*Cl$_2$]$_2$ (2.5 mol %), [e]added [CoCp*(CO)I$_2$] (5 mol %) instead of [RhCp*Cl$_2$]$_2$ (2.5 mol %), [f]added [RhCp*Cl$_2$]$_2$ (1 mol %))
— Yield was derived by flash column chromatography.

Succinimide has been used as a carbonyl electrophile in intermolecular and intramolecular coupling reactions. Therefore, the present inventors planned the intramolecular cyclization of the synthetic compound 3aa under reducing reaction conditions in order to prepare the oxindole 3a. As shown in chemical reaction Formula 2 and table 2, it was confirmed that the combination of Zn powder and AcOH in EtOH solvent at room temperature after the screening of the reaction conditions, yielded oxindole 3a in 91% yield.

[Chemical reation Formula 2]

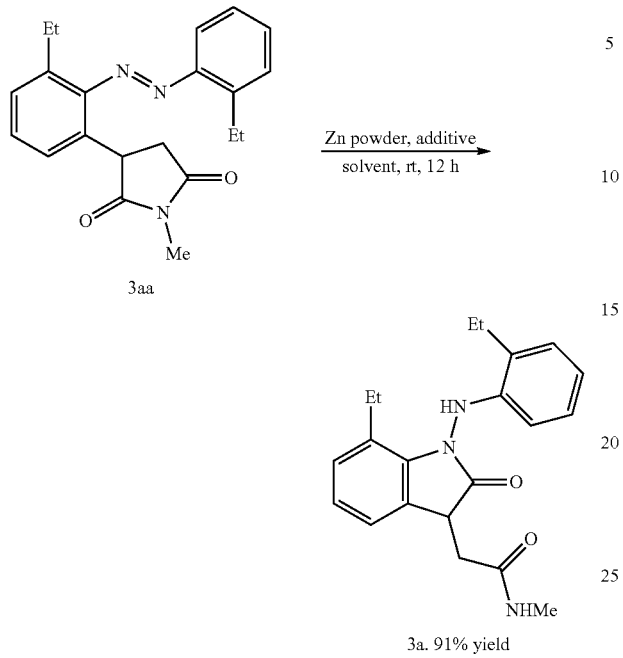

3aa. 91% yield

TABLE 2

| Entry | Additive (equiv.) | Solvent | Yield[a, b] |
|---|---|---|---|
| 1 | AcOH (5) | EtOH | N.R. |
| 2 | AcOH (5) | EtOH | 91 |
| 3 | NH₄Cl(5) | EtOH | 85 |
| 4 | AcOH (5) | DCE | N.R. |
| 5 | AcOH (5) | MeOH | 90 |
| 6 | AcOH (5) | H₂O | 50 |
| 7 | AcOH (5) | EtOH | 75 |
| 8 | AcOH (3) | EtOH | 80 |
| 9 | AcOH (6) | EtOH | 92. |

Based on these results, one-pot C—H alkylation and intramolecular cyclization of azobenzene 1a was further performed with maleimide 2a. In particular, after the C—H alkylation reaction, the reaction mixture was directly treated without further purification of 3aa under reductive cyclization conditions. Satisfactory, as shown in chemical reaction Formula 3 below, the production of oxindole product 3a was observed with good yield (72%).

[Chemical reation Formula 3]

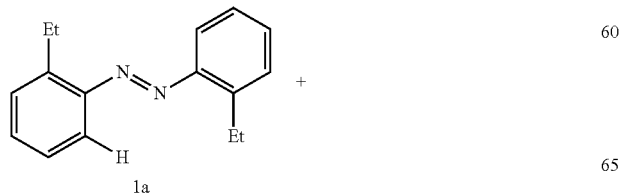

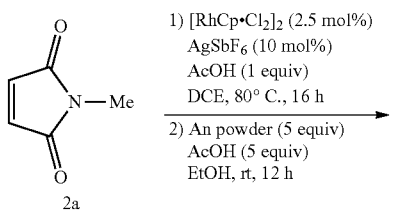

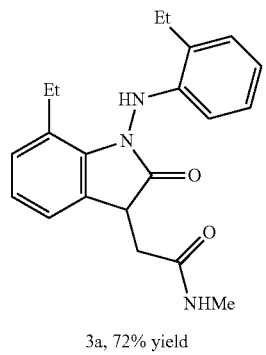

3a, 72% yield

Example 2

Figure 3:
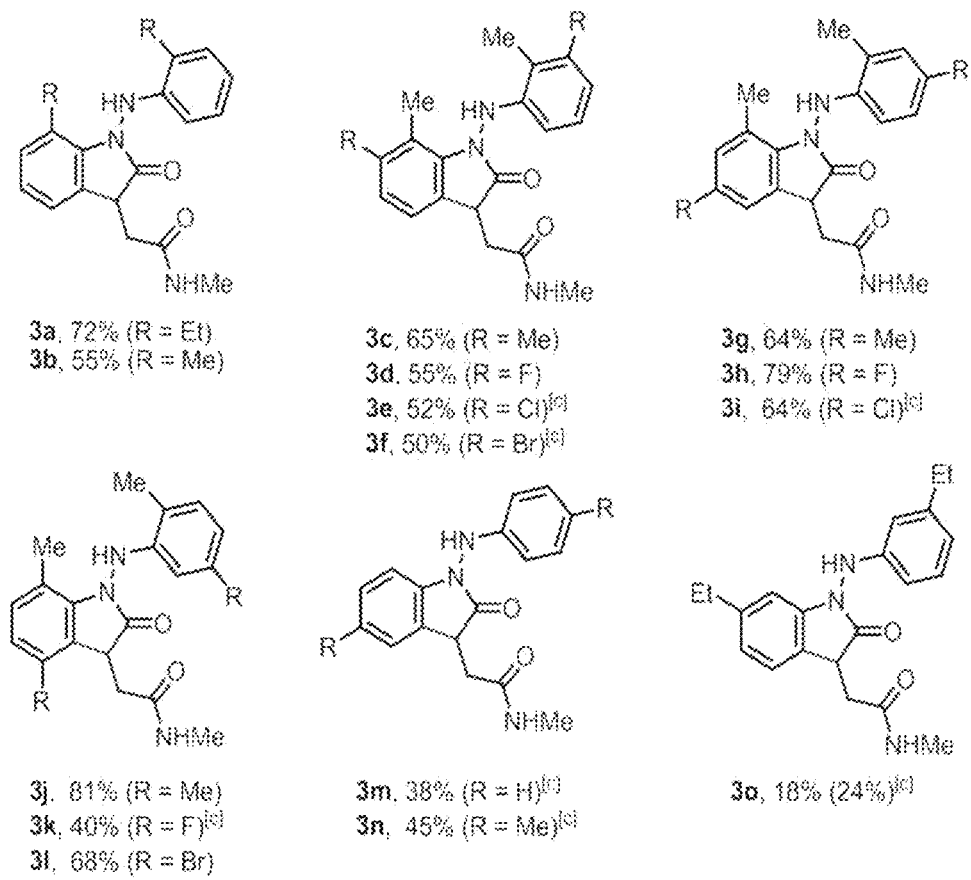
FIG. 3 shows the oxindole derivatives synthesized using various azobenzene compounds and yields.

Synthesis of Oxindole Derivatives Via Various Azobenzene Coupling Reactions At the optimum conditions of the coupling reaction determined in example 1, coupling reactions of various compounds were carried out. More specifically, various azobenzenes (1a to 1o) were reacted with maleimide (2a) as shown in chemical reaction Formula 4 below. The resulting products (3a to 3o) and their yields are shown in FIG. 3.

[Chemical reation Formula 4]

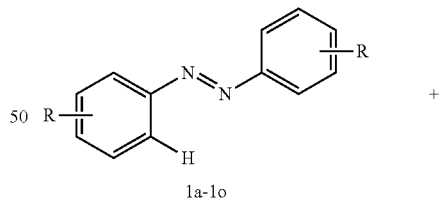

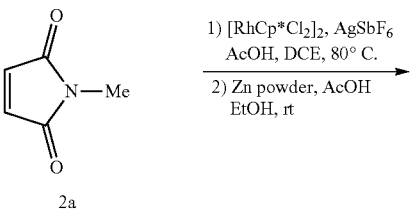

-continued

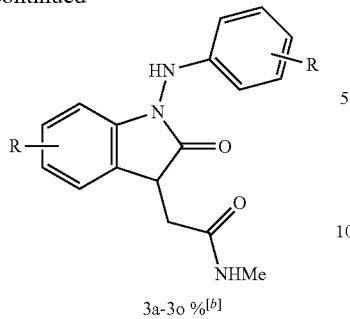

3a-3o %[b]

Reaction conditions: 1) 1a-1o (0.2 mmol), 2a (0.3 mmol), [RhCp*Cl₂]₂ (2.5 mol %), AgSbF₆ (10 mol %), AcOH (1 eq), DCE (0.5 mL), reaction in pressure tubes for 16 hours at 80° C., some alkylation steps are performed at 100° C. 2) Zinc powder (Zn powder, 5 eq.), AcOH (5 eq.), EtOH (1 mL), reaction at room temperature for 12 hours The reaction of ortho-methyl-substituted azobenzene 1b provided the desired product 3b in 55% yield. In addition, 2,3-disubstituted azobenzene (1c-1f) was also coupled with 2a to provide the corresponding oxindole (3c-3f) in reasonable yield or in good yield. Furthermore, the 2,4-disubstituted azobenzene (1g-1i) showed very similar reactivity to give the oxindole adduct 3g-3i. Surprisingly, this modification gives the corresponding product 3j in a yield of 81% by the 2,5-disubstituted azobenzene 1j with steric hindrance, while the 2,5-disubstituted azobenzene 1k and 1l containing the electron incomplete group at the C5-position were found to be less reactive to the formation of oxindoles 3k and 3l.

It was also confirmed that the symmetrical azobenzene (1m and 1n) also undergoes C—H alkylation and reductive cyclization to provide oxindoles (3m and 3n). Surprisingly, it has been found that meta-substituted azobenzene (1o) exhibits significantly reduced reactivity despite much effort in optimizing the reaction conditions, leading to the formation of an inseparable mixture of undiscovered impurities and 3o.

Example 3

Synthesis of Oxindole Derivatives Through Coupling of Various Maleimides

To evaluate the range of maleimide reactants, the ring forming reaction of various maleimides (2b to 2j) and azobenzene (1a) was carried out, as shown in chemical reaction Formula 5 below.

[Chemical reaction Formula 5]

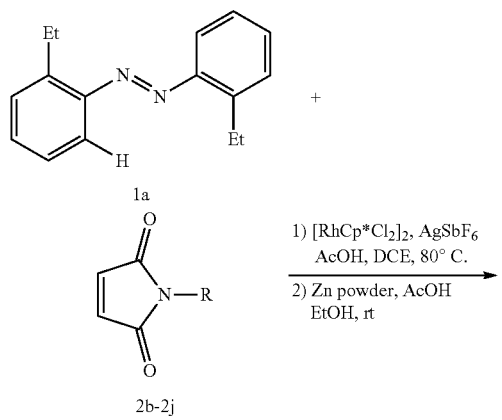

-continued

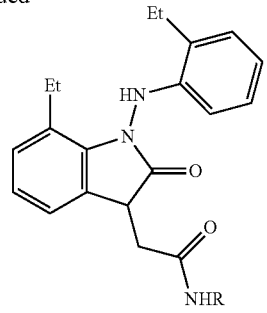

4b-4j, %[b]

Figure 4:
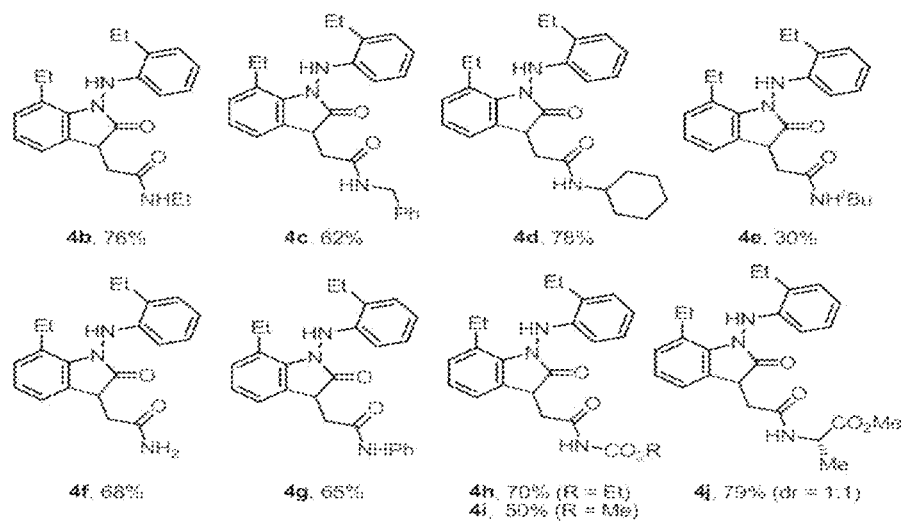
FIG. 4 shows the oxindole derivatives synthesized using various maleimide compounds and yields.

Reaction conditions: 1) 1a (0.2 mmol), 2b-2j (0.3 mmol), [RhCp*Cl₂]₂ (2.5 mol %), AgSbF₆ (10 mol %), AcOH (1 eq), DCE (0.5 mL), reaction in pressure tubes for 16 hours at 80° C.; 2) Zinc powder (Zn powder, 5 eq.), AcOH (5 eq.), EtOH (1 mL), reaction at room temperature for 12 hours As a result, the obtained products and their yields are shown in FIG. 4. Linear and branched alkyl-substituted maleimides 2b-2d were found to be advantageous in obtaining a high yield of the desired product 4b-4d in the coupling reaction. However, N-tert-butyl maleimide 2e showed low reactivity under the present reaction conditions. In addition, the unprotected and N-aryl maleimides 2f and 2g were identified as excellent substrates for providing the corresponding products 4f and 4g. In particular, it can be seen that the reaction can proceed readily with N-carboxylate maleimides 2h and 2i to yield oxindoles 4h and 4i in moderate to good yields. The remaining acyl carbamate moieties can provide a multifunctional synthetic function for multi-layer synthesis. In addition, the conversion showed high reactivity in the coupling reaction of maleimide 2j derived from the corresponding amino acid and chemically delivered 4j in 79% yield with a 1:1 diastereomer ratio.

Example 4

Confirmation of Chemical Selectivity Using Asymmetric Azobenzene

Figure 5:
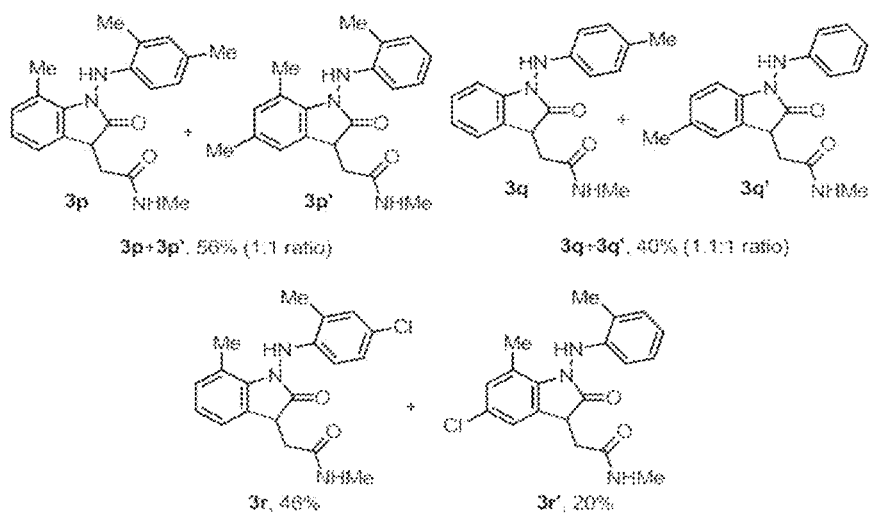
FIG. 5 shows the oxindole derivatives synthesized using asymmetric azobenzene and yields.

In order to confirm the chemical selectivity in the reaction of the present invention, the intramolecular competition reaction of asymmetric azobenzene 1p-1r and 2a was confirmed as shown in chemical reaction Formula 6 below. The resulting products and yields are shown in FIG. 5. As can be seen in FIG. 5, 3p and 3p' were obtained with a 56% yield in the case of 1p, and were present in a ratio of 1:1, and 1q was similarly obtained with a 40% yield and in a 1.1:1 ratio, no significant difference between the ratios was observed. However, the para-Cl-substituted azobenzene 1r was obtained in a yield of 66% with a 2.3:1 ratio of product.

[Chemical reation Formula 6]

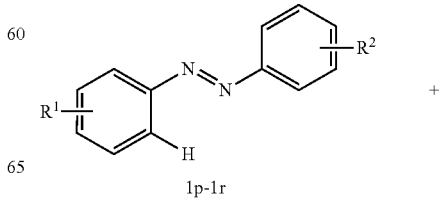

1p-1r

-continued

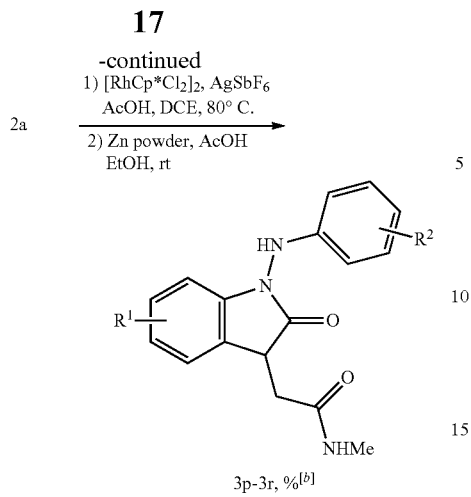

3p-3r, %[b]

Reaction conditions: 1) 1p-1r (0.2 mmol), 2a (0.3 mmol), [RhCp*Cl₂]₂ (2.5 mol %), AgSbF₆ (10 mol %), AcOH (1 eq), DCE (0.5 mL), reaction in pressure tubes for 16 hours at 80° C.; Zinc powder (Zn powder, 5 eq.), AcOH (5 eq.), EtOH (1 mL), reaction at room temperature for 12 hours

Example 5

Confirmation of the Synthesis of Oxindole Using Internal Olefin

Figure 6:
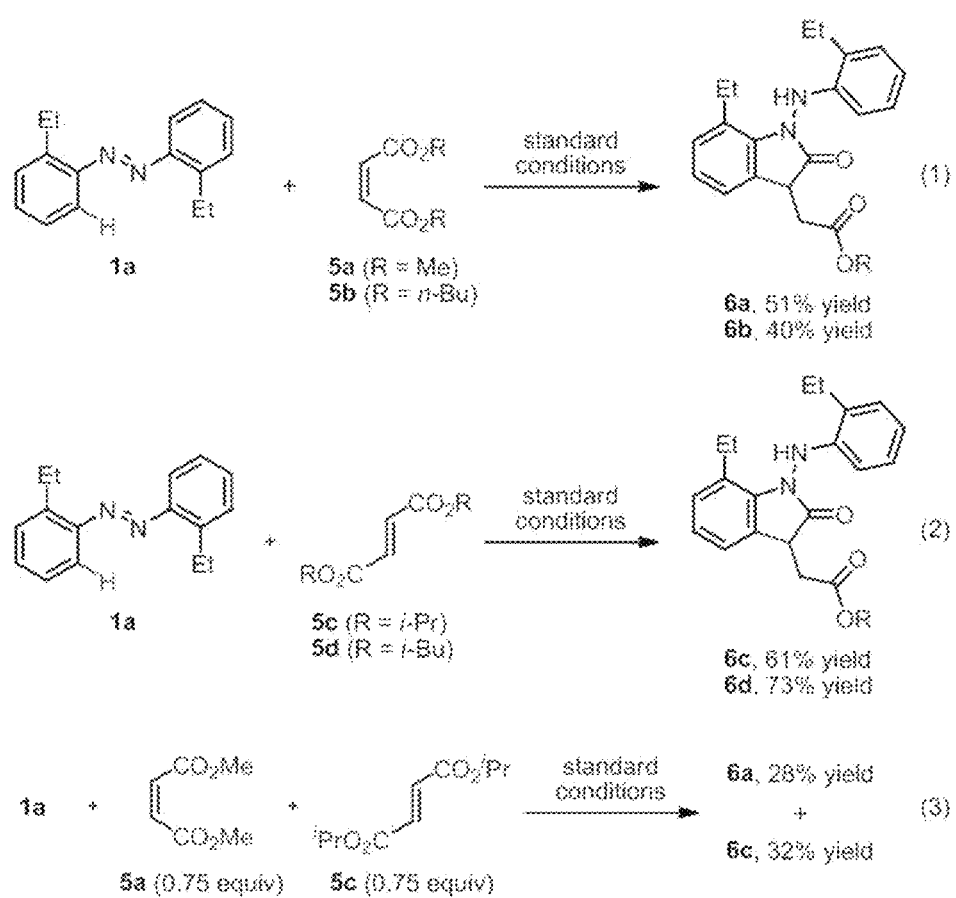
FIG. 6 shows the oxindole derivatives synthesized using malate and fumarate and yields.

On the other hand, from the results of one-pot synthesis of oxindole using maleimide, in this Example, it was confirmed that oxindole is formed by using other internal olefin such as maleate and fumarate as shown in FIG. 6. The internal cis-olefins 5a and 5b were obtained as oxindoles 6a and 6b via C—H alkylation and reduction reactions. Surprisingly, it has been found that fumarates 5c and 5d as internal trans-olefins are able to participate in the coupling reaction smoothly to provide the corresponding oxindole products 6c and 6d in good yield. Competition experiments between 5a and 5c resulted in 28% of oxindole 6a and 32% of 6c.

Interestingly, applying the Cu(OAc)₂ additive instead of AcOH while further optimizing the coupling reaction between azobenzene and the internal olefin, as shown in chemical reaction Formula 7 below, unexpected 2,3-disubstituted indole 7a was obtained at 60% by the reaction of azobenzene 1o with n-butyl maleate (5b) under cationic Rh (III) catalysis. This reaction probably results in the nucleophilic addition of the C—Rh bond on the intermediate to the N═N bond of the azobenzene which can undergo NN bond cleavage, followed by aromatization under oxidizing conditions to give the free-(NH)-indole product 7a.

[Chemical reation Formula 7]

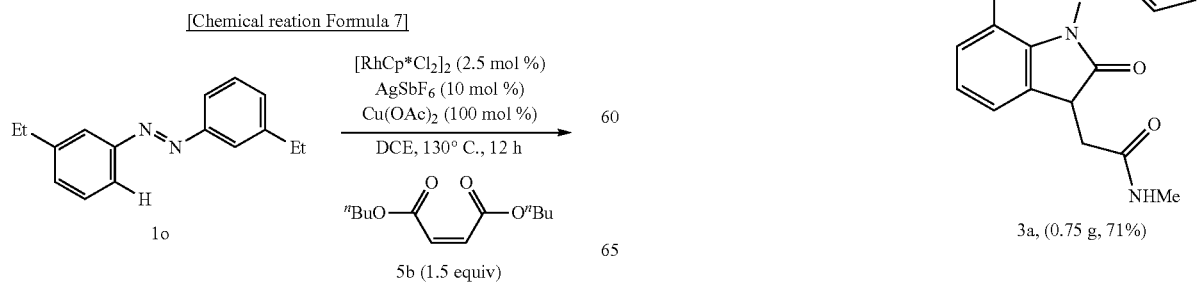

-continued

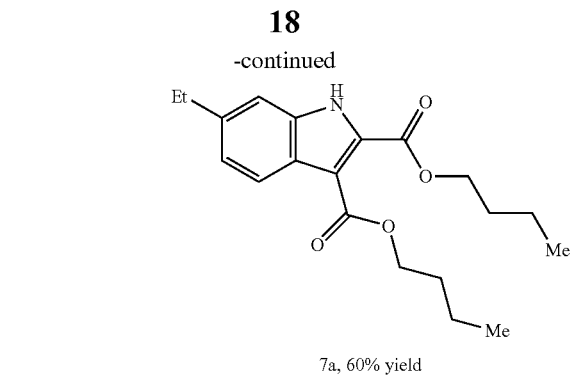

7a, 60% yield

Example 6

Confirmation of Mass Production Possibility and Usability of Oxindole Synthesis In order to confirm that the scale of synthesis in the oxindole method of the present invention can be enlarged, oxindole was prepared by increasing azobenzene to 3 mmol. As a result, 0.75 g of 3a was obtained in 71% yield under optimum reaction conditions as shown in chemical reaction Formula 8.

In order to demonstrate the usefulness of 1-aminooxindole, following chemical reaction Formula 9 attempts to cleave NH-aryl groups at 3a and 6c under Raney Ni-mediated reduction conditions to yield free-(NH)-oxindoles 8a and 8b.

[Chemical reation Formula 8]

scale-up experiment

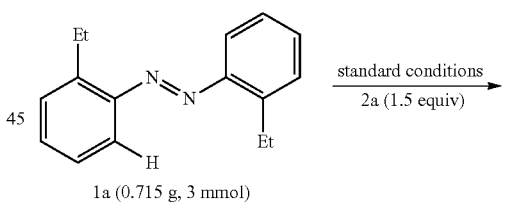

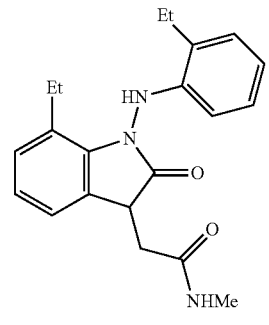

3a, (0.75 g, 71%)

19

-continued
[Chemical reation Formula 9]
synthetic transformations

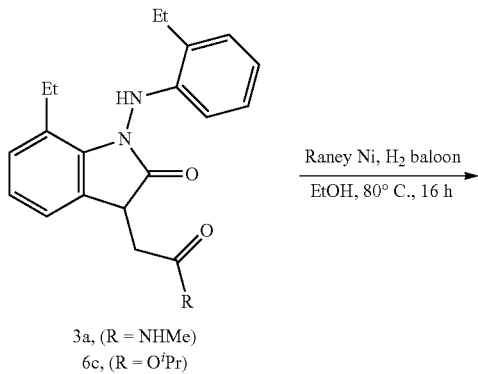

3a, (R = NHMe)
6c, (R = O$^i$Pr)

8a, 51% yield
8b, 64% yield

Example 7

Confirmation of Mechanism of Oxindole Formation

To confirm the mechanism, two parallel reactions of 2a, 1m and deuterio-1m were performed under standard reaction conditions as shown in chemical reaction Formula 10 below, and the reaction isotope effect (kH/kD) was 3.17, confirming that C—H bond cleavage can be included in the rate determination step.

[Chemical reation Formula 10]

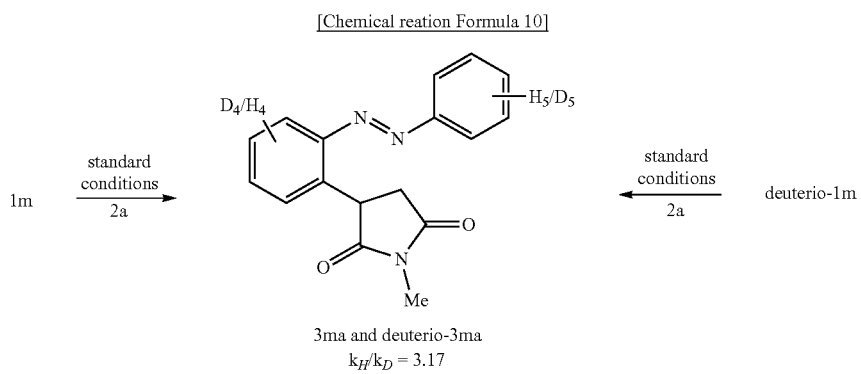

3ma and deuterio-3ma
$k_H/k_D = 3.17$

Figure 7:
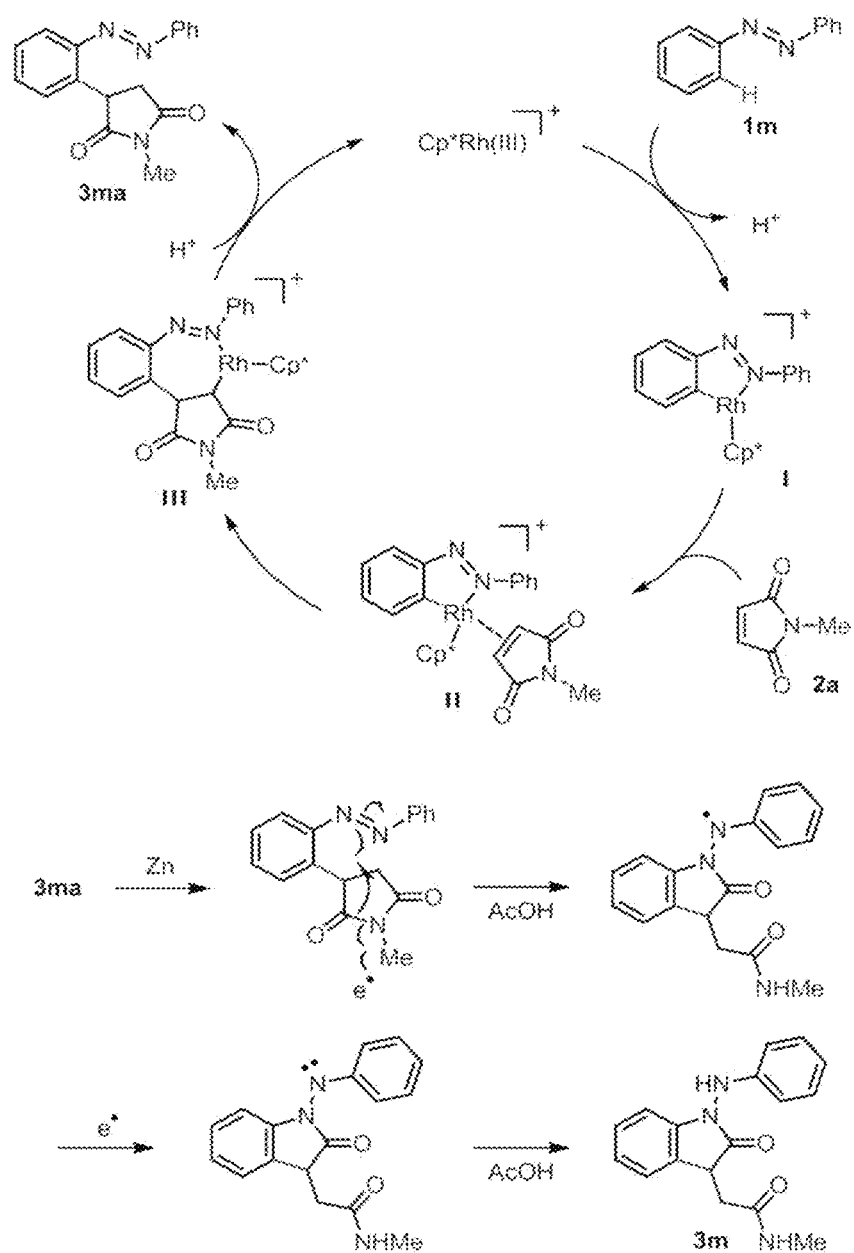
FIG. 7 shows the anticipated mechanism of the oxindole formation reaction through the C—H alkylation of the present invention and the subsequent reductive intramolecular cyclization.

Thus, the mechanism path for the preparation method of the present invention is shown in FIG. 7. The 1m azo group can be coordinated with the cationic Rh (III) catalyst, and the subsequent C—H cleavage can produce a five-membered Rhodacycle I. The maleimide (2a) is then coordinated with complex I to provide intermediate II, which is transferred into the Rh—N bond to form Rhodacycle species III.

20

Protonation of rhodacycle species III provides ortho-alkylated azobenzene 3ma. The reductive cyclization of 3 ma with Zn and AcOH was proposed to include areneazo radical intermediates to deliver 3 m of oxindole product.

In conclusion, FIG. 7 shows the generation mechanism of the present invention, wherein the present invention is to synthesize oxindoles by C—H alkylation and reductive cyclization of azobenzene and internal olefins (For example, maleimide, maleate and fumarate) by positional Rh (III) catalysts. By such synthesis, C3 functionalized oxindole derivatives can be synthesized. In particular, the reductive cleavage of the NH-aryl group in the oxindole formed using Raney Ni and H$_2$ gas provided free-(NH)-oxindole.

Also, unexpected 2,3-disubstituted indoles could be synthesized by the coupling reaction of azobenzene and maleate in the presence of Cu(OAc)$_2$ additive.

Example 8

Structural Analysis of New Compounds by NMR Analysis 8.1. Synthesis of Oxindole Derivatives Using Maleimide as Substrate
8.1.1.
Formation and structural analysis of 2-(7-Ethyl-1-((2-ethylphenyl)amino)-2-oxoindolin-3-yl)-N-methylacetamide (3a)
[RhCp*Cl$_2$]$_2$ (3.1 mg, 0.005 mmol, 2.5 mol %), AgSbF$_6$ (6.9 mg, 0.02 mmol, 10 mol %) and AcOH (12.0 mg, 0.2 mmol, 100 mol %) were mixed in an oven dried sealed tube charged with 1,2-bis(2-ethylphenyl)diazine (1a) (47.7 mg, 0.2 mmol, 100 mol %). Then, 1-methyl-1H-pyrrole (2a) (33.3 mg, 0.3 mmol, 150 mol %) and DCE (0.5 mL) were treated and reacted at room temperature and air. The reaction mixture was stirred at 80° C. for 16 hours, and after cooling the reaction mixture to room temperature, Zn powder (65.4 mg, 1.0 mmol, 500 mol %), AcOH (60.0 mg, 1.0 mmol, 500 mol %) and EtOH (1 ml) were added to the resulting reaction mixture without any further purification or post processing. After the reaction mixture was stirred at room temperature for 12 hours, the reaction mixture was filtered, washed with dichloromethane (20 mL) and concentrated in vacuo. The residue was purified by flash column chromatography (n-Hexane/EtOAc=1:3) to give 3a (50.6 mg) in 72% yield. The production of the following 3a to 3r, 4b to 4j and 6a to 6d was also prepared in accordance with the above conditions.

[Formula 3a]

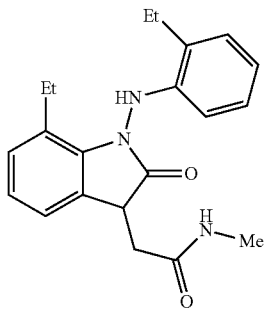

50.6 mg (72%); white solid; mp=182.8-185.3° C.; $^1$H NMR (400 MHz, CDCl$_3$) δ7.18-7.16 (m, 2H), 7.10 (d, J=8.0 Hz, 1H), 7.06-7.01 (m, 2H), 6.90 (t, J=7.2 Hz, 1H), 6.58-6.55 (m, 2H), 6.46 (br s, 1H), 3.93 (t, J=6.0 Hz, 1H), 2.85 (dd, J=15.2, 6.4 Hz, 1H), 2.78 (d, J=4.8 Hz, 3H), 2.75-2.63 (m, 5H), 1.33 (t, J=7.2 Hz, 3H), 1.13 (t, J=7.6 Hz, 3H); $^{13}$C NMR (100 MHz, CDCl$_3$) δ177.2, 170.4, 144.0, 139.7, 130.4, 128.9, 128.8, 127.3, 127.0, 126.4, 123.4, 121.9, 121.7, 111.9, 40.6, 37.1, 26.4, 23.8, 23.4, 16.4, 13.3; IR (KBr) υ 3298, 3100, 3060, 2965, 2932, 2872, 2360, 1713, 1652, 1604, 1588, 1509, 1455, 1410, 1375, 1295, 1213, 1165, 1137, 1063, 933, 743 cm$^{-1}$; HRMS (quadrupole, EI) calcd for C$_{21}$H$_{25}$N$_3$O$_2$[M]$^+$ 351.1947, found 351.1947.

8.1.2. Formation and structural analysis of N-Methyl-2-(7-methyl-2-oxo-1-(o-tolylamino)indolin-3-yl)acetamide (3b)

[Formula 3b]

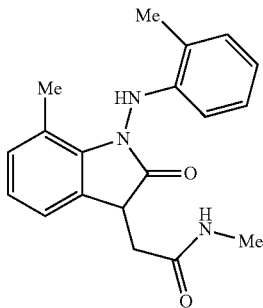

35.8 mg (55%); white solid; mp=190.2-193.7° C.; $^1$H NMR (400 MHz, CDCl$_3$) δ7.16-7.11 (m, 2H), 7.05-6.97 (m, 3H), 6.85 (t, J=7.6 Hz, 1H), 6.56 (d, J=7.6 Hz, 1H), 6.44 (br s, 2H), 3.91 (t, J=6.4 Hz, 1H), 2.86 (dd, J=15.6, 6.4 Hz, 1H), 2.76 (d, J=4.8 Hz, 3H), 2.67 (dd, J=15.2, 5.6 Hz, 1H), 2.34 (s, 3H), 2.30 (s, 3H); $^{13}$C NMR (100 MHz, CDCl$_3$) δ177.1, 170.4, 144.6, 140.4, 131.9, 130.7, 127.1, 126.3, 123.2, 122.9, 121.8, 121.4, 120.8, 111.6, 40.6, 36.9, 26.4, 17.0, 16.7; IR (KBr) υ 3296, 3095, 3055, 2963, 2931, 2347, 1711, 1654, 1589, 1557, 1462, 1410, 1380, 1326, 1296, 1266, 1219, 1162, 1136, 1049, 990, 738 cm$^{-1}$; HRMS (orbitrap, ESI) calcd for C$_{19}$H$_{21}$N$_3$O$_2$ [M+H]$^+$ 324.1718, found 324.1707.

8.1.3. Formation and structural analysis of 2-(1-((2,3-Dimethylphenyl)amino)-6,7-dimethyl-2-oxoindolin-3-yl)-N-methylacetamide (3c)

[Formula 3c]

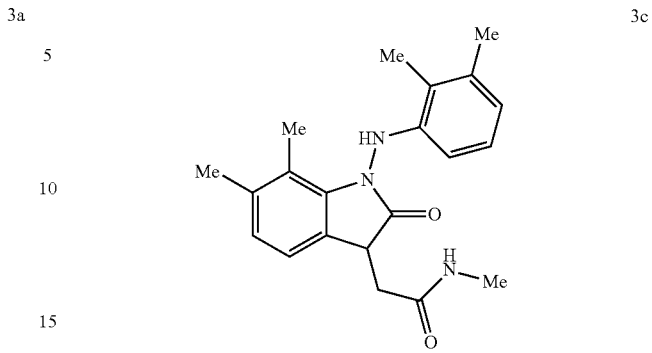

45.9 mg (65%); white solid; mp=172.2-174.3° C.; $^1$H NMR (400 MHz, CDCl$_3$) δ7.04 (d, J=7.6 Hz, 1H), 6.92-6.89 (m, 2H), 6.77 (d, J=7.6 Hz, 1H), 6.55 (br s, 2H), 6.43 (br s, 1H), 3.85 (t, J=6.4 Hz, 1H), 2.80 (dd, J=15.2, 6.4 Hz, 1H), 2.74 (d, J=4.8 Hz, 3H), 2.67-2.63 (m, 1H), 2.29 (s, 3H), 2.28 (s, 3H), 2.25 (s, 3H), 2.19 (s, 3H); $^{13}$C NMR (100 MHz, CDCl$_3$) δ177.5, 170.5, 144.5, 140.2, 138.5, 137.2, 126.2, 124.7, 124.2, 123.5, 121.6, 121.2, 120.0, 109.9, 40.2, 37.1, 26.3, 20.4, 20.2, 12.3, 11.7; IR (KBr) υ 3304, 3056, 2923, 2854, 2362, 2341, 1715, 1653, 1617, 1589, 1558, 1472, 1412, 1267, 1211, 1174, 1098, 989, 815, 768, 741 cm$^{-1}$; HRMS (orbitrap, ESI) calcd for C$_{21}$H$_{26}$N$_3$O$_2$ [M+H]$^+$ 352.2020, found 352.2030.

8.1.4. Formation and structural analysis of 2-(6-Fluoro-1-((3-fluoro-2-methylphenyl)amino)-7-methyl-2-oxoindolin-3-yl)-N-methylacetamide (3d)

[Formula 3d]

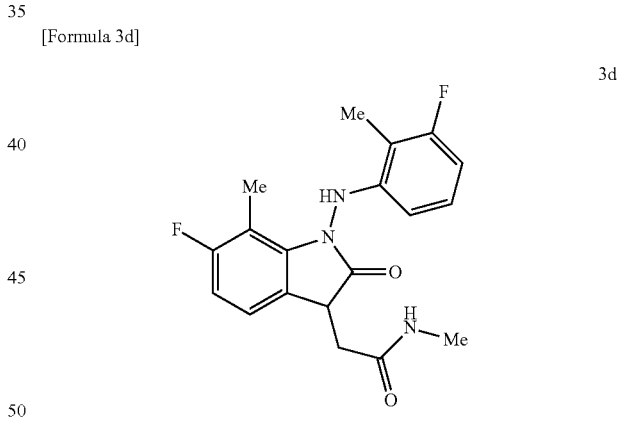

39.7 mg (55%); White solid; mp=231.3-233.1° C.; $^1$H NMR (400 MHz, CDCl$_3$) δ7.10 (br s, 1H), 7.04-6.98 (m, 1H), 6.77 (t, J=8.4 Hz, 1H), 6.67 (t, J=8.8 Hz, 1H), 6.40-6.38 (m, 2H), 5.94 (br s, 1H), 3.87 (t, J=6.4 Hz, 1H), 2.88 (dd, J=15.6, 5.6 Hz, 1H), 2.80 (d, J=4.8 Hz, 3H), 2.71 (br s, 1H), 2.24 (d, J=6.8 Hz, 6H); $^{13}$C NMR (100 MHz, CDCl$_3$) δ 177.3, 169.9, 161.7 (d, J$_{C-F}$=279.0 Hz), 161.6 (d, J$_{C-F}$=204.1 Hz), 146.1, 141.5, 127.4 (d, J$_{C-F}$=10.2 Hz), 121.7 (d, J$_{C-F}$=71.2 Hz), 117.5 (d, J$_{C-F}$=22.5 Hz), 110.4 (d, J$_{C-F}$=19.8 Hz), 109.7 (d, J$_{C-F}$=22.4 Hz), 109.4 (d, J$_{C-F}$=24.4 Hz), 108.5 (d, J$_{C-F}$=23.5 Hz), 107.4 (d, J$_{C-F}$=2.7 Hz), 40.1, 36.7, 26.5, 8.1 (d, J$_{C-F}$=6.0 Hz), 7.6 (d, J$_{C-F}$=5.9 Hz); IR (KBr) υ 3292, 3100, 2921, 2852, 1709, 1652, 1619, 1591, 1468, 1377, 1240, 1220, 1156, 1093, 1071, 815, 773, 735 cm$^{-1}$; HRMS (quadrupole, EI) calcd for C$_{19}$H$_{19}$F$_2$N$_3$O$_2$[H]$^+$ 359.1445, found 359.1443.

8.1.5. Formation and structural analysis of 2-(6-Chloro-1-((3-chloro-2-methylphenyl)amino)-7-methyl-2-oxoindolin-3-yl)-N-methylacetamide (3e)

[Formula 3e]

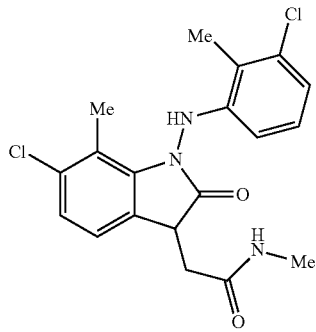

3e 38.7 mg (49%); white solid; mp=98.6-100.2° C.; $^1$H NMR (400 MHz, CDCl$_3$) δ 7.12 (d, J=8.0 Hz, 1H), 7.07 (d, J=8.0 Hz, 1H), 7.00-6.95 (m, 2H), 6.65 (br s, 1H), 6.50 (d, J=6.8 Hz, 1H), 6.02 (br s, 1H), 3.84 (t, J=6.0 Hz, 1H), 2.86 (dd, J=15.6, 5.6 Hz, 1H), 2.75 (br s, 4H), 2.39 (s, 3H), 2.34 (s, 3H); $^{13}$C NMR (100 MHz, CDCl$_3$) δ 177.2, 169.9, 145.7, 141.3, 136.1, 135.2, 127.3, 125.0, 124.1, 122.6, 122.1, 121.3, 119.7, 110.4, 40.1, 36.4, 26.4, 13.2, 12.6; IR (KBr) υ 3296, 2921, 2853, 2360, 1703, 1654, 1602, 1579, 1459, 1377, 1276, 1164, 1119, 1071, 1012, 864, 773, 736 cm$^{-1}$; HRMS (orbitrap, ESI) calcd for C$_{19}$H$_{20}$C$_{12}$N$_3$O$_2$ [M+H]$^+$ 392.0927, found 392.0946.

8.1.6. Formation and structural analysis of 2-(6-Bromo-1-((3-bromo-2-methylphenyl)amino)-7-methyl-2-oxoindolin-3-yl)-N-methylacetamide (3f)

[Formula 3f]

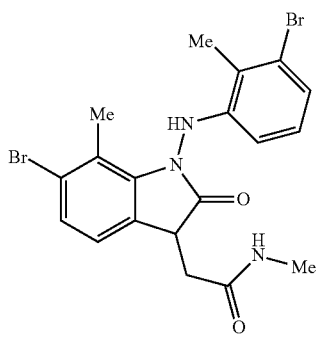

3f 46.5 mg (48%); brown sticky solid; $^1$H NMR (400 MHz, CDCl$_3$) δ 7.32 (d, J=7.6 Hz, 1H), 7.17 (d, J=7.6 Hz, 1H), 7.01 (d, J=7.2 Hz, 1H), 6.90 (t, J=8.0 Hz, 1H), 6.66 (br s, 1H), 6.54 (d, J=8.0 Hz, 1H), 6.01 (br s, 1H), 3.80 (t, J=6.0 Hz, 1H), 2.86 (dd, J=15.6, 5.6 Hz, 1H), 2.75 (br s, 4H), 2.43 (s, 3H), 2.38 (s, 3H); $^{13}$C NMR (100 MHz, CDCl$_3$) δ 176.8, 169.8, 145.6, 141.2, 127.8, 127.4, 127.1, 126.1, 125.9, 125.8, 122.9, 122.5, 121.2, 111.1, 40.1, 36.3, 26.4, 16.4, 15.7; IR (KBr) υ 3309, 3093, 2923, 2854, 2362, 1703, 1654, 1594, 1573, 1455, 1440, 1375, 1265, 1174, 999, 809, 735 cm$^{-1}$; HRMS (quadrupole, EI) calcd for C$_{19}$H$_{19}$Br$_2$N$_3$O$_2$ [M]$^+$ 478.9844, found 478.9845.

8.1.7. Formation and structural analysis of 2-(1-((2,4-Dimethylphenyl)amino)-5,7-dimethyl-2-oxoindolin-3-yl-N-methylacetamide (3g)

[Formula 3g]

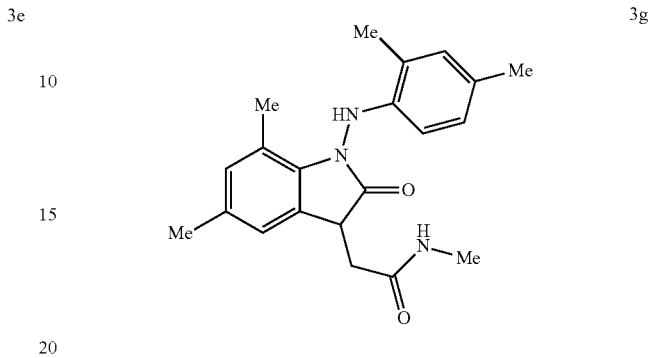

3g 45.1 mg (64%); white solid; mp=190.8-193.3° C.; $^1$H NMR (400 MHz, CDCl$_3$) δ 6.98 (s, 1H), 6.95 (s, 1H), 6.84-6.82 (m, 2H), 6.55 (br s, 1H), 6.44 (d, J=8.4 Hz, 1H), 6.32 (s, 1H), 3.87 (t, J=6.4 Hz, 1H), 2.83 (dd, J=15.6, 6.8 Hz, 1H), 2.78 (d, J=4.8 Hz, 3H), 2.65 (dd, J=15.6, 6.0 Hz, 1H), 2.30 (s, 3H), 2.28 (d, J=2.8 Hz, 6H), 2.22 (s, 3H); $^{13}$C NMR (100 MHz, CDCl$_3$) δ 177.0, 170.5, 142.3, 137.9, 132.7, 132.3, 131.4, 130.7, 127.4, 126.4, 122.9, 122.6, 120.4, 111.8, 40.7, 37.1, 26.4, 20.9, 20.4, 16.9, 16.5; IR (KBr) υ 3310, 3052, 3009, 2921, 2855, 2734, 2364, 1710, 1652, 1613, 1555, 1509, 1475, 1410, 1366, 1335, 1265, 1220, 1158, 1136, 1071, 1037, 988, 857, 807, 735 cm$^{-1}$; HRMS (orbitrap, ESI) calcd for C$_{21}$H$_{26}$N$_3$O$_2$ [M+H]$^+$ 352.2020, found 352.2034.

8.1.8. Formation and structural analysis of 2-(5-Fluoro-1-((4-fluoro-2-methylphenyl)amino)-7-methyl-2-oxoindolin-3-yl)-N-methylacetamide (3h)

[Formula 3h]

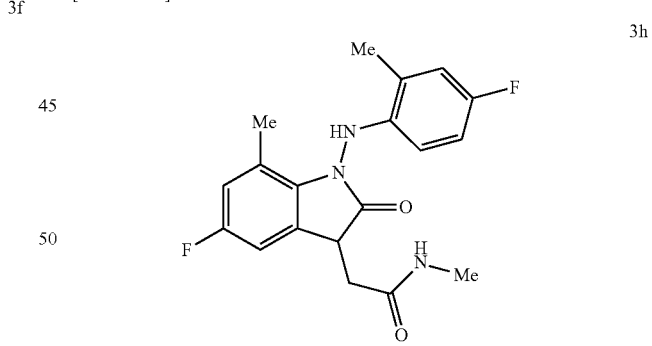

3h 56.9 mg (79%); white solid; mp=161.2-163.4° C.; $^1$H NMR (400 MHz, CDCl$_3$) δ 6.90-6.83 (m, 2H), 6.76-6.71 (m, 2H), 6.55-6.51 (m, 1H), 6.43 (br s, 1H), 6.14 (br s, 1H), 3.85 (t, J=6.0 Hz, 1H), 2.87 (dd, J=15.6, 5.6 Hz, 1H), 2.74 (d, J=4.8 Hz, 3H), 2.70 (dd, J=15.6, 6.4 Hz, 1H), 2.30 (s, 3H), 2.24 (s, 3H); $^{13}$C NMR (100 MHz, CDCl$_3$) δ 176.7, 169.8, 159.1 (d, J$_{C-F}$=239.8 Hz), 157.8 (d, J$_{C-F}$=237.4 Hz), 140.5 (d, J$_{C-F}$=2.0 Hz), 136.2, 128.0 (d, J$_{C-F}$=8.8 Hz), 125.1 (d, J$_{C-F}$=7.4 Hz), 122.3 (d, J$_{C-F}$=7.5 Hz), 118.0 (d, J$_{C-F}$=22.6 Hz), 117.4 (d, J$_{C-F}$=22.6 Hz), 113.1 (d, J$_{C-F}$=22.1 Hz), 112.8 (d, J$_{C-F}$=8.2 Hz), 109.5 (d, J$_{C-F}$=24.5 Hz), 40.8, 36.3, 26.4, 17.1, 16.6; IR (KBr) υ 3309, 3109, 2922, 2853, 2367, 1714, 1651, 1623, 1557, 1491, 1476, 1412, 1371, 1338, 1267, 1238, 1202, 1153, 1129, 1070, 999, 979, 952, 862, 806, 736 cm$^{-1}$; HRMS (orbitrap, ESI) calcd for C$_{19}$H$_{20}$F$_2$N$_3$O$_2$ [M+H]$^+$ 360.1518, found 360.1530.

8.1.9. Formation and structural analysis of 2-(5-Chloro-1-((4-chloro-2-methylphenyl)amino)-7-methyl-2-oxoindolin-3-yl)-N-methylacetamide (3i)

[Formula 3i]

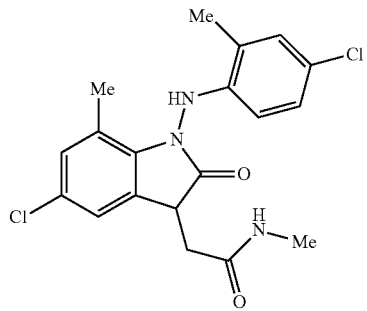

3i 50.3 mg (64%); white solid; mp=185.5-188.2° C.; $^1$H NMR (400 MHz, CDCl$_3$) δ7.12 (d, J=6.4 Hz, 2H), 7.03-7.01 (m, 2H), 6.54 (d, J=8.4 Hz, 1H), 6.38 (br s, 1H), 5.89 (br s, 1H), 3.85 (t, J=6.0 Hz, 1H), 2.88 (dd, J=16.0, 5.2 Hz, 1H), 2.79-2.77 (m, 4H), 2.28 (d, J=11.2 Hz, 6H); $^{13}$C NMR (100 MHz, CDCl$_3$) δ176.4, 169.7, 143.2, 139.1, 131.5, 130.5, 128.3, 128.1, 126.9, 126.3, 124.9, 122.2, 122.1, 113.1, 40.5, 36.2, 26.5, 16.9, 16.5; IR (KBr) υ 3273, 3055, 2985, 2359, 2329, 1730, 1651, 1403, 1365, 1267, 1217, 1144, 1029, 806, 742 cm$^{-1}$; HRMS (orbitrap, ESI) calcd for C$_{19}$H$_{20}$OCl$_2$N$_3$O$_2$ [M+H]$^+$ 392.0927, found 392.0944.

8.1.10. Formation and structural analysis of 2-(1-((2,5-Dimethylphenyl)amino)-4,7-dimethyl-2-oxoindolin-3-yl)-N-methylacetamide (3i)

[Formula 3j]

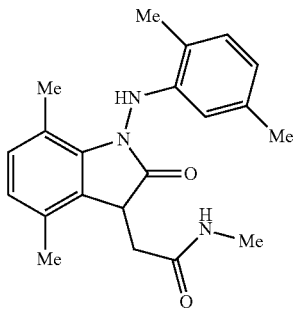

3j 57.2 mg (81%); white solid; mp=206.8-209.3° C.; $^1$H NMR (500 MHz, CDCl$_3$) δ6.99 (d, J=7.5 Hz, 1H), 6.95 (d, J=8.0 Hz, 1H), 6.82 (d, J=7.5 Hz, 1H), 6.66 (d, J=7.5 Hz, 2H), 6.40-6.34 (m, 2H), 3.82 (br s, 1H), 2.98 (d, J=14.5 Hz, 1H), 2.76-2.71 (m, 4H), 2.36 (s, 3H), 2.31 (s, 3H), 2.26 (s, 3H), 2.18 (s, 3H); $^{13}$C NMR (125 MHz, CDCl$_3$) δ 177.4, 170.3, 144.4, 140.5, 136.8, 131.9, 131.8, 130.5, 125.1, 123.9, 122.1, 119.9, 118.3, 112.3, 40.4, 35.8, 26.3, 21.3, 18.2, 16.7, 16.5; IR (KBr) υ 3307, 3098, 3050, 2921, 2362, 1709, 1654, 1618, 1583, 1521, 1459, 1412, 1323, 1246, 1160, 1068, 1038, 857, 799, 734 cm$^{-1}$; HRMS (orbitrap, ESI) calcd for C$_{21}$H$_{26}$N$_3$O$_2$ [M+H]$^+$ 352.2020, found 352.2034.

8.1.11. Formation and structural analysis of 2-(4-Fluoro-1-((5-fluoro-2-methylphenyl)amino)-7-methyl-2-oxoindolin-3-yl)-N-methylacetamide (3k)

[Formula 3k]

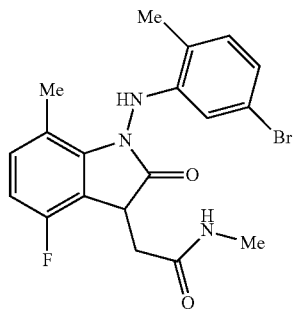

3k 27.5 mg (38%); white solid; mp=139.1-141.6° C.; $^1$H NMR (400 MHz, CDCl$_3$) δ7.03-6.95 (m, 2H), 6.72-6.65 (m, 2H), 6.53 (td, J=8.0, 2.4 Hz, 1H), 6.31 (br s, 1H), 5.97 (br s, 1H), 3.85 (t, J=4.8 Hz, 1H), 3.12-3.09 (m, 1H), 2.96 (dd, J=15.2, 5.6 Hz, 1H), 2.65 (br s, 3H), 2.26 (s, 3H), 2.16 (br s, 3H); $^{13}$C NMR (100 MHz, CDCl$_3$) δ176.5, 169.7, 162.4 (d, J$_{C-F}$=242.1 Hz), 157.2 (d, J$_{C-F}$=242.4 Hz), 146.1, 142.1, 133.1 (d, J$_{C-F}$=8.0 Hz), 131.4 (d, J$_{C-F}$=8.6 Hz), 118.2, 116.5, 111.8 (d, J$_{C-F}$=21.0 Hz), 109.9 (d, J$_{C-F}$=20.4 Hz), 107.3, 99.4, 38.8, 34.7, 26.2, 16.3, 16.2; IR (KBr) υ 3309, 3056, 2923, 2854, 2358, 1714, 1654, 1616, 1501, 1459, 1412, 1378, 1267, 1243, 1158, 1101, 1066, 1004, 967, 869, 795, 742 cm$^{-1}$; HRMS (orbitrap, ESI) calcd for C$_{19}$H$_{20}$F$_2$N$_3$O$_2$ [M+H]$^+$ 360.1518, found 360.1530.

8.1.12. Formation and structural analysis of 2-(4-Bromo-1-((5-bromo-2-methylphenyl)amino)-7-methyl-2-oxoindolin-3-yl)-N-methylacetamide (3l)

[Formula 3l]

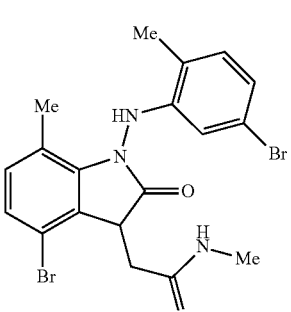

3l 65.4 mg (68%); white solid; mp=144.0-146.9° C.; $^1$H NMR (400 MHz, CDCl$_3$) δ7.09 (d, J=8.0 Hz, 1H), 6.95-6.89 (m, 3H), 6.68 (br s, 1H), 5.89 (br s, 1H), 3.71 (s, 1H), 3.33 (dd, J=15.6, 5.6 Hz, 1H), 3.18 (dd, J=15.6, 2.8 Hz, 1H), 3.85 (t, J=6.4 Hz, 1H), 2.63 (s, 3H), 2.27 (s, 3H), 2.16 (s, 3H); $^{13}$C NMR (100 MHz, CDCl$_3$) 176.4, 169.8, 146.1, 142.9, 133.5, 131.9, 126.3, 125.1, 124.0, 121.9, 120.4, 120.0, 115.9, 114.5, 41.9, 34.3, 26.3, 16.7, 16.6; IR (KBr) υ 3311, 3095, 3063, 2923, 2854, 2347, 1780, 1698, 1657, 1588, 1475, 1408, 1276, 1249, 1220, 1116, 1047, 996, 943, 883, 795, 736 cm$^{-1}$; HRMS (quadrupole, EI) calcd for C$_{19}$H$_{19}$Br$_2$N$_3$O$_2$ [M]$^+$ 478.9844, found 478.9845.

8.1.13. Formation and structural analysis of N-Methyl-2-(2-oxo-1-(benzylamino)indolin-3-yl)acetamide (3m)

[Formula 3m]

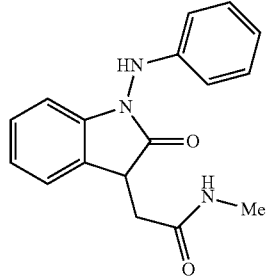

3m 15.6 mg (26%); white solid; mp=100.7-103.2° C.; $^1$H NMR (400 MHz, CDCl$_3$) δ 7.32 (d, J=7.6 Hz, 1H), 7.26 (t, J=7.6 Hz, 1H), 7.22-7.18 (m, 2H), 7.09 (t, J=7.6 Hz, 1H), 6.97 (d, J=8.0 Hz, 1H), 6.92 (t, J=7.6 Hz, 1H), 6.78-6.75 (m, 2H), 6.56 (br s, 1H), 6.24 (br s, 1H), 3.96 (t, J=6.4 Hz, 1H), 2.90 (dd, J=15.6, 6.0 Hz, 1H), 2.77 (d, J=4.8 Hz, 3H), 2.68 (dd, J=15.6, 7.2 Hz, 1H); $^{13}$C NMR (100 MHz, CDCl$_3$) δ 176.5, 170.3, 145.8, 143.2, 129.4, 128.6, 125.9, 124.3, 123.4, 121.7, 113.5, 108.9, 41.2, 36.8, 26.4; IR (KBr) υ 3283, 3055, 2922, 2852, 1707, 1652, 1601, 1540, 1463, 1410, 1303, 1265, 1174, 1100, 1026, 991, 841, 734 cm$^{-1}$; HRMS (orbitrap, ESI) calcd for C$_{17}$H$_{18}$N$_3$O$_2$ [M+H]$^+$ 296.1394, found 296.1404.

8.1.14. Formation and structural analysis of N-Methyl-2-(5-methyl-2-oxo-1-(p-tolylamino)indolin-3-yl)acetamide (3n)

[Formula 3n]

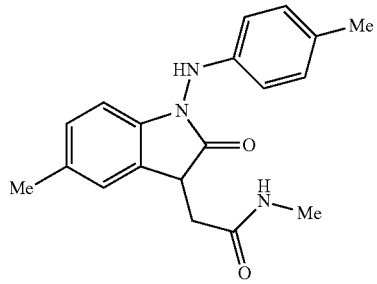

3n 29.2 mg (45%); yellow sticky solid; $^1$H NMR (400 MHz, CDCl$_3$) δ 7.14 (s, 1H), 7.05 (d, J=8.0 Hz, 1H), 6.99 (d, J=8.0 Hz, 2H), 6.84 (d, J=7.6 Hz, 1H), 6.67 (d, J=8.4 Hz, 2H), 6.46 (s, 1H), 6.37 (br s, 1H), 3.91 (t, J=6.4 Hz, 1H), 2.87 (dd, J=15.6, 6.0 Hz, 1H), 2.78 (d, J=4.8 Hz, 3H), 2.64 (dd, J=15.6, 7.2 Hz, 1H), 2.32 (s, 3H), 2.24 (s, 3H); $^{13}$C NMR (100 MHz, CDCl$_3$) 176.4, 170.4, 143.4, 140.8, 133.0, 131.1, 129.8, 128.8, 125.1, 113.7, 108.7, 41.2, 36.9, 26.4, 21.2, 20.5; IR (KBr) υ 3282, 3109, 2922, 2853, 2359, 1712, 1649, 1512, 1487, 1410, 1375, 1331, 1240, 1211, 1123, 1040, 943, 810, 734 cm$^{-1}$; HRMS (orbitrap, ESI) calcd for C19H$_{22}$N$_3$O$_2$ [M+H]$^+$ 324.1707, found 324.1719.

8.1.15. Formation and structural analysis of 2-(6-Ethyl-1-((3-ethylphenyl)amino)-2-oxoindolin-3-yl)-N-methylacetamide (3o)

[Formula 3o]

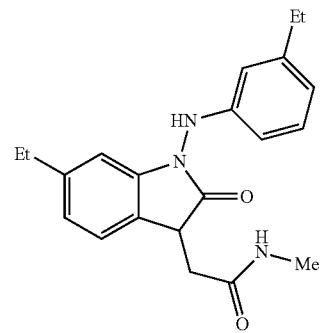

3o 10.7 mg (15%); white solid; mp=79.7-81.1° C.; $^1$H NMR (400 MHz, CDCl$_3$) δ 7.23 (d, J=8.0 Hz, 1H), 7.12 (t, J=7.6 Hz, 1H), 6.92 (dd, J=7.6, 1.6 Hz, 1H), 6.85 (s, 1H), 6.78 (d, J=7.6 Hz, 1H), 6.65 (br s, 1H), 6.55 (dd, J=8.0, 2.0 Hz, 1H), 6.44 (br s, 1H), 6.32 (br s, 1H), 3.92 (t, J=6.8 Hz, 1H), 2.88 (dd, J=15.6, 6.4 Hz, 1H), 2.79 (d, J=4.8 Hz, 3H), 2.67-2.54 (m, 5H), 1.19 (t, J=7.2 Hz, 3H), 1.17 (t, J=7.6 Hz, 3H); $^{13}$C NMR (100 MHz, CDCl$_3$) δ 176.9, 170.4, 145.9, 145.7, 145.4, 143.4, 129.3, 124.2, 123.1, 122.8, 121.4, 113.2, 110.7, 108.5, 41.0, 37.1, 29.1, 28.8, 26.5, 15.6, 15.3; IR (KBr) υ 3283, 2963, 2923, 2359, 2340, 1710, 1698, 1652, 1626, 1558, 1455, 1368, 1261, 1165, 1122, 1063, 862, 762 cm$^{-1}$; HRMS (orbitrap, ESI) calcd for C$_{21}$H$_{26}$N$_3$O$_2$ [M+H]$^+$ 352.2020, found 352.2032.

8.1.16. Formation and structural analysis of 2-(1-(2,4-Dimethylphenylamino)-7-methyl-2-oxoindolin-3-yl)-N-methylacetamide (3p) and 2-(5,7-dimethyl-2-oxo-1-(o-tolylamino)indolin-3-yl)-N-methylacetamide (3p')

[Formula 3p]

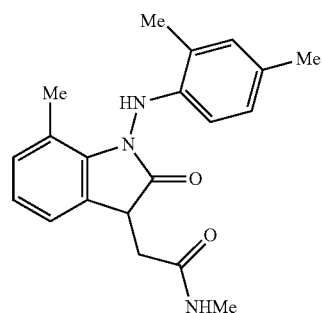

3p

[Formula 3p']

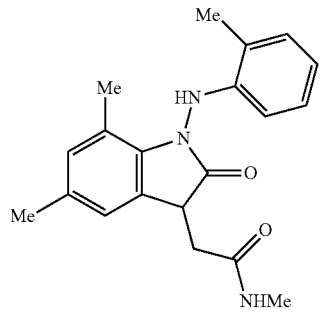

3p'

37.8 mg (56%); white solid; mp=155.8-157.6° C.; $^1$H NMR (400 MHz, CDCl$_3$) δ 7.15 (d, J=6.8 Hz, 1H), 7.11 (d, J=7.6 Hz, 1H), 7.04-6.94 (m, 5H), 6.86-6.83 (m, 3H), 6.55-6.37 (m, 6H), 3.91-3.85 (m, 2H), 2.87-2.81 (m, 2H), 2.77-2.76 (m, 6H), 2.68-2.62 (m, 2H), 2.35 (s, 3H), 2.29 (s, 9H), 2.27 (s, 3H), 2.23 (s, 3H); $^{13}$C NMR (100 MHz, CDCl$_3$) δ177.1, 177.0, 170.5, 170.4, 144.6, 152.3, 150.5, 137.9, 132.7, 132.3, 131.9, 131.5, 130.7, 130.6, 127.4, 127.1, 126.5, 126.4, 123.1, 123.0, 122.9, 122.6, 121.8, 121.3, 120.8, 120.4, 111.8, 111.6, 40.7, 40.6, 37.0 (two carbon overlap), 26.4 (two carbon overlap), 20.9, 20.5, 17.0, 16.9, 16.7, 16.5; IR (KBr) υ 3296, 2922, 2853, 2359, 1708, 1651, 1611, 1557, 1509, 1463, 1410, 1377, 1330, 1265, 1220, 1195, 1049, 989, 858, 808, 734 cm$^{-1}$; HRMS (orbitrap, ESI) calcd for C$_{20}$H$_{24}$N$_3$O$_2$ [M+H]$^+$ 338.1863, found 338.1866.

8.1.17. Formation and structural analysis of N-Methyl-2-(2-oxo-1-(g-tolylamino)indolin-3-yl)acetamide (3q) and N-methyl-2-(5-methyl-2-oxo-1-(phenylamino)indolin-3-yl) acetamide (3q')

[Formula 3q]

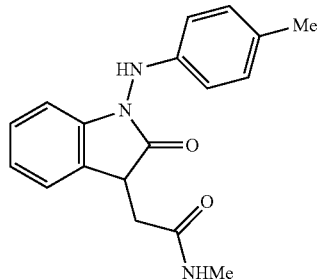

3q

[Formula 3q']

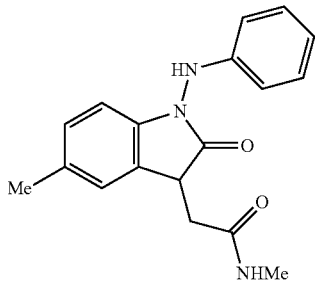

3q'

24.7 mg (40%); yellow sticky solid; $^1$H NMR (400 MHz, CDCl$_3$) δ 7.29 (d, J=6.2 Hz, 1H), 7.24 (t, J=8.0 Hz, 1H), 7.19-7.15 (m, 2H), 7.13 (br s, 1H), 7.07-7.02 (m, 2H), 6.99-6.93 (m, 3H), 6.88 (t, J=7.6 Hz, 1H), 6.82 (d, J=7.6 Hz, 1H), 6.74-6.72 (m, 3H), 6.67-6.65 (m, 3H), 6.42 (br s, 2H), 3.93-3.88 (m, 2H), 2.89-2.83 (m, 2H), 2.73-2.71 (m, 6H), 2.66-2.60 (m, 2H), 2.31 (s, 3H), 2.23 (s, 3H); $^{13}$C NMR (100 MHz, CDCl$_3$) δ 176.6, 176.5, 170.5, 170.4, 145.8, 143.4, 143.3, 140.7, 132.9, 130.9, 129.8, 129.3, 128.7, 128.5, 126.0, 125.9, 125.1, 124.2, 123.2, 121.4, 113.6, 113.4, 108.9, 108.6, 41.2 (two carbon overlap), 36.6 (two carbon overlap), 26.4 (two carbon overlap), 21.1, 20.5; IR (KBr) υ 3268, 3054, 2923, 2854, 2360, 2341, 1714, 1652, 1618, 1513, 1463, 1410, 1332, 1266, 1175, 1126, 990, 811, 738 cm$^{-1}$; HRMS (orbitrap, ESI) calcd for C$_{18}$H$_{20}$N$_3$O$_2$ [M+H]$^+$ 310.1550, found 310.1552.

8.1.18. Formation and structural analysis of 2-(1-(4-Chloro-2-methylphenylamino)-7-methyl-2-oxoindolin-3-yl)-N-methylacetamide (3r)

[Formula 3r]

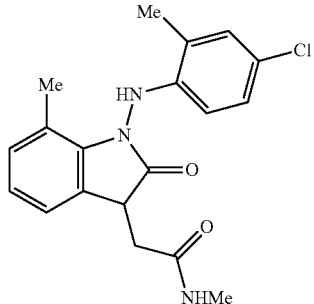

3r 33.1 mg (46%); white solid; mp=174.2-176.9° C.; $^1$H NMR (400 MHz, CDCl$_3$) δ7.13 (d, J=6.8 Hz, 1H), 7.09 (s, 1H), 7.02-6.96 (m, 3H), 6.52 (d, J=8.8 Hz, 2H), 6.26 (br s, 1H), 3.88 (t, J=6.4 Hz, 1H), 2.85 (dd, J=15.6, 6.0 Hz, 1H), 2.73-2.68 (m, 4H), 2.30 (s, 3H), 2.22 (s, 3H); $^{13}$C NMR (100 MHz, CDCl$_3$) δ177.1, 170.2, 143.4, 140.2, 131.9, 130.4, 126.8, 126.4, 126.0, 124.8, 123.2, 121.7, 120.7, 112.9, 40.6, 36.7, 26.4, 16.9, 16.6; IR (KBr) υ3296, 3097, 3053, 2922, 2853, 2356, 1710, 1651, 1556, 1482, 1463, 1410, 1378, 1327, 1297, 1265, 1219, 1185, 1141, 1071, 1039, 992, 887, 808, 732 cm$^{-1}$; HRMS (orbitrap, ESI) calcd for C$_{19}$H$_{21}$ClN$_3$O$_2$ [M+H]$^+$ 358.1317, found 358.1324.

8.1.19. Formation and structural analysis of 2-(5-Chloro-7-methyl-2-oxo-1-(o-tolylamino)indolin-3-yl)-N-methylacetamide (3r')

[Formula 3r']

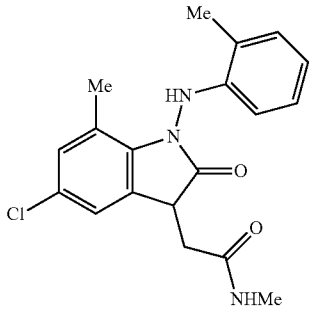

3r'

14.4 mg (20%); white solid; mp=174.9-177.3° C.; $^1$H NMR (400 MHz, CDCl$_3$) δ7.15-7.12 (m, 2H), 7.07-7.02 (m, 2H), 6.87 (t, J=7.2 Hz, 1H), 6.55 (d, J=8.0 Hz, 1H), 6.36 (s, 1H), 6.00 (br s, 1H), 3.89 (t, J=6.0 Hz, 1H), 2.89 (dd, J=15.6, 5.2 Hz, 1H), 2.79 (d, J=4.8 Hz, 3H), 2.71 (br s, 1H), 2.31 (s, 6H); $^{13}$C NMR (100 MHz, CDCl$_3$) δ 176.4, 169.8, 144.5, 139.2, 131.5, 130.8, 128.2, 128.1, 127.2, 123.1, 122.3, 122.1, 121.6, 111.7, 40.6, 36.5, 26.5, 17.1, 16.6; IR (KBr) υ 3310, 3058, 2921, 2852, 2360, 1714, 1654, 1607, 1590, 1557, 1462, 1411, 1376, 1244, 1159, 1118, 1049, 996, 939, 862, 750 cm$^{-1}$; HRMS (orbitrap, ESI) calcd for C$_9$H$_{21}$ClN$_3$O$_2$ [M+H]$^+$ 358.1317, found 358.1322.

8.1.20. Formation and structural analysis of N-Ethyl-2-(7-ethyl-1-((2-ethylphenyl)amino)-2-oxoindolin-3-yl)acetamide (4b)

[Formula 4b]

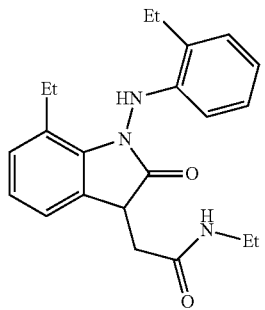

4b 55.7 mg (76%); white solid; mp=146.5-147.5° C.; $^1$H NMR (400 MHz, CDCl$_3$) δ7.17 (t, J=7.6 Hz, 2H), 7.09 (d, J=7.2 Hz, 1H), 7.06-7.01 (m, 2H), 6.90 (t, J=7.6 Hz, 1H), 6.60-6.56 (m, 2H), 6.35 (br s, 1H), 3.94 (t, J=6.4 Hz, 1H), 3.31-3.24 (m, 2H), 2.86 (dd, J=15.6, 6.4 Hz, 1H), 2.72-2.58 (m, 5H), 1.33 (t, J=7.6 Hz, 3H), 1.15-1.09 (m, 6H); $^{13}$C NMR (100 MHz, CDCl$_3$) δ177.0, 169.6, 144.0, 139.7, 130.4, 128.9, 128.7, 127.3, 126.9, 126.5, 123.3, 121.9, 121.6, 111 0.9, 40.5, 37.3, 34.6, 23.8, 23.4, 16.4, 14.7, 13.3; IR (KBr) υ 3308, 3052, 2973, 2931, 2874, 2375, 1709, 1659, 1605, 1589, 1541, 1509, 1455, 1378, 1295, 1264, 1212, 1164, 1064, 979, 935, 848, 732 cm$^{-1}$; HRMS (orbitrap, ESI) calcd for C$_{22}$H$_{28}$N$_3$O$_2$ [M+H]$^+$ 366.2176, found 366.2188.

8.1.21. Formation and structural analysis of N-Benzyl-2-(7-ethyl-1-((2-ethylphenyl)amino)-2-oxoindolin-3-yl)acetamide (4c)

[Formula 4c]

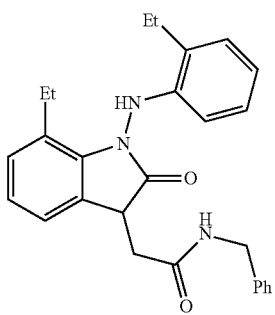

4c 50.7 mg (59%); white solid; mp=103.2-104.8° C.; $^1$H NMR (400 MHz, CDCl$_3$) δ 7.32-7.22 (m, 5H), 7.17-7.15 (m, 2H), 7.10 (d, J=7.6 Hz, 1H), 7.03 (d, J=7.2 Hz, 2H), 6.90 (t, J=7.6 Hz, 1H), 6.60-6.53 (m, 3H), 4.43 (br s, 2H), 3.96 (t, J=6.0 Hz, 1H), 2.92 (dd, J=15.6, 6.0 Hz, 1H), 2.71-2.66 (m, 5H), 1.33 (t, J=7.6 Hz, 3H), 1.13 (t, J=7.6 Hz, 3H); $^{13}$C NMR (100 MHz, CDCl$_3$) δ 176.9, 169.6, 144.0, 139.7, 138.0, 130.4, 128.9, 128.7, 128.6, 127.8, 127.4, 127.3, 127.0, 126.3, 123.3, 122.0, 121.7, 111.9, 43.7, 40.5, 37.2, 23.8, 23.4, 16.4, 13.3; IR (KBr) υ3284, 2978, 2732, 2351, 1739, 1650, 1405, 1367, 1267, 1222, 1149, 1029, 809, 744 cm$^{-1}$; HRMS (orbitrap, ESI) calcd for C$_{27}$H$_{30}$N$_3$O$_2$ [M+H]$^+$ 428.2333, found 428.2343.

8.1.22. Formation and structural analysis of N-Cyclohexyl-2-(7-ethyl-1-((2-ethylphenyl)amino)-2-oxoindolin-3-yl)acetamide (4d)

[Formula 4d]

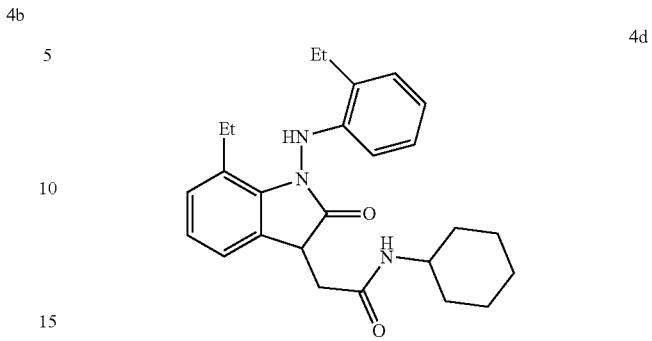

4d 65.5 mg (78%); white solid; mp=91.9-94.4° C.; $^1$H NMR (400 MHz, CDCl$_3$) δ 7.27 (d, J=7.2 Hz, 1H), 7.11-7.10 (m, 2H), 7.05 (d, J=7.6 Hz, 1H), 7.01 (t, J=7.6 Hz, 1H), 6.88 (t, J=7.2 Hz, 1H), 6.82 (s, 1H), 6.55 (br s, 1H), 5.93 (br s, 1H), 3.76 (br s, 1H), 2.75-2.48 (m, 6H), 1.86 (br s, 2H), 1.69-1.57 (m, 3H), 1.31-1.20 (m, 6H), 1.11-1.06 (m, 6H); $^{13}$C NMR (100 MHz, CDCl$_3$) δ 175.9, 169.2, 143.9, 138.9, 132.0, 129.1, 128.5, 127.8, 126.8, 123.8, 121.7, 121.5, 111.5, 72.6, 48.5, 41.7, 32.8, 32.6, 25.3, 24.8, 24.7, 23.5, 23.4, 16.3, 13.1; IR (KBr) υ 3285, 2925, 2853, 2368, 1710, 1638, 1540, 1453, 1380, 1292, 1264, 1221, 1164, 1066, 890, 738 cm$^{-1}$; HRMS (quadrupole, EI) calcd for C$_{26}$H$_{33}$N$_3$O$_2$ [M]$^+$ 419.2573, found 419.2570.

8.1.23. Formation and structural analysis of N-(tert-Butyl)-2-(7-ethyl-1-((2-ethylenyl)amino)-2-oxoindolin-3-yl)acetamide (4e)

[Formula 4e]

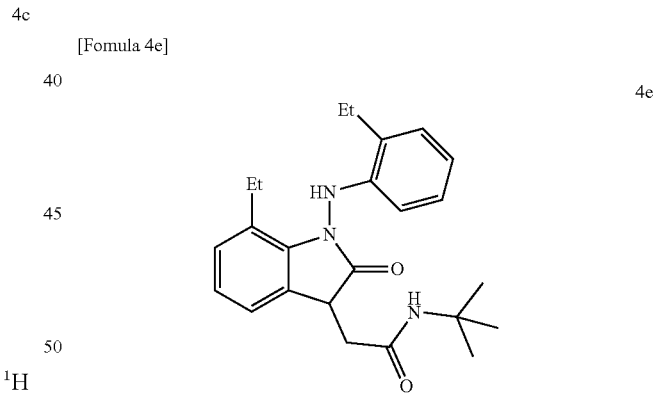

4e 23.8 mg (30%); yellow sticky solid; $^1$H NMR (400 MHz, CDCl$_3$) δ 7.21-7.16 (m, 2H), 7.10-7.02 (m, 3H), 6.91 (t, J=7.2 Hz, 1H), 6.53 (br s, 2H), 5.92 (br s, 1H), 3.98 (t, J=6.0 Hz, 1H), 2.86 (dd, J=14.8, 5.6 Hz, 1H), 2.73-2.68 (m, 4H), 2.46 (br s, 1H), 1.36 (s, 12H), 1.32 (t, J=7.6 Hz, 3H); $^{13}$C NMR (100 MHz, CDCl$_3$) δ 176.9, 168.9, 144.1, 139.7, 130.4, 129.0, 128.7, 127.2, 127.0, 126.8, 123.3, 122.2, 121.7, 112.0, 51.5, 40.7, 38.5, 28.7, 23.8, 23.4, 16.5, 13.3; IR (KBr) υ 3323, 3059, 2965, 2927, 2871, 2361, 1712, 1658, 1607, 1543, 1509, 1454, 1392, 1294, 1266, 1220, 1164, 1136, 1065, 962, 850, 745 cm$^{-1}$; HRMS (orbitrap, ESI) calcd for C$_{24}$H$_{32}$N$_3$O$_2$ [M+H]$^+$ 394.2489, found 394.2502.

8.1.24. Formation and structural analysis of 2-(7-Ethyl-1-((2-ethylphenyl)amino)-2-oxoindolin-3-yl)acetamide (4f)

[Formula 4f]

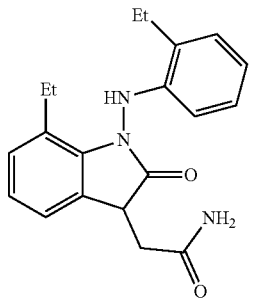

4f 46.1 mg (68%); white solid; mp=183.7-185.3° C.; $^1$H NMR (400 MHz, CDCl$_3$) δ 7.20-7.15 (m, 2H), 7.11-7.01 (m, 3H), 6.90 (t, J=7.6 Hz, 1H), 6.61-6.59 (m, 2H), 6.37 (br s, 1H), 3.90 (br s, 1H), 2.89 (dd, J=15.6, 6.0 Hz, 1H), 2.72-2.66 (m, 5H), 1.33 (t, J=7.2 Hz, 3H), 1.13 (t, J=7.6 Hz, 3H); $^{13}$C NMR (100 MHz, CDCl$_3$) δ 177.0, 172.2, 144.1, 139.7, 130.5, 128.9, 128.7, 127.3, 127.0, 126.3, 123.4, 121.9, 121.7, 111.9, 40.3, 36.5, 23.8, 23.4, 16.4, 13.4; IR (KBr) υ 3310, 3063, 2963, 2923, 2871, 2365, 1714, 1652, 1605, 1542, 1514, 1454, 1376, 1296, 1246, 1211, 1165, 1137, 1063, 1028, 964, 745 cm$^{-1}$; HRMS (orbitrap, ESI) calcd for Cl$_{20}$H$_{24}$N$_3$O$_2$ [M+H]$^+$ 338.1863, found 338.1876.

8.1.25. Formation and structural analysis of 2-(7-Ethyl-1-((2-ethylphenyl)amino)-2-oxoindolin-3-yl)-N-phenylacetamide (4g)

[Formula 4g]

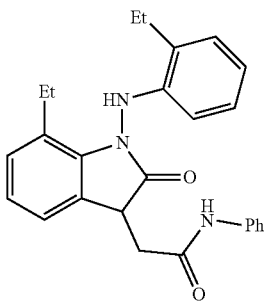

4g 53.9 mg (65%); white solid; mp=191.5-194.2° C.; $^1$H NMR (400 MHz, CDCl$_3$) δ 8.66 (br s, 1H), 7.52 (d, J=8.0 Hz, 2H), 7.29 (t, J=7.6 Hz, 2H), 7.24 (t, J=8.4 Hz, 1H), 7.16 (d, J=7.6 Hz, 1H), 7.13-7.05 (m, 3H), 6.90 (br s, 2H), 6.58 (br s, 2H), 4.02 (t, J=6.0 Hz, 1H), 3.05 (dd, J=15.6, 7.2 Hz, 1H), 2.84-2.68 (m, 5H), 1.34 (t, J=7.6 Hz, 3H), 1.14 (t, J=7.6 Hz, 3H); $^{13}$C NMR (100 MHz, CDCl$_3$) δ 177.3, 168.1, 143.9, 139.5, 137.9, 130.7, 129.0, 128.9, 128.8, 127.5, 127.1, 126.2, 124.2, 123.7, 122.1, 121.9, 119.9, 111.8, 40.5, 38.6, 23.8, 23.4, 16.4, 13.3; IR (KBr) υ 3309, 3267, 3142, 3052, 2958, 2922, 2853, 2365, 1715, 1674, 1598, 1549, 1497, 1454, 1442, 1376, 1297, 1251, 1220, 1144, 1064, 1032, 964, 901, 748 cm$^{-1}$; HRMS (orbitrap, ESI) calcd for C$_{26}$H$_{28}$N$_3$O$_2$ [M+H]$^+$ 414.2176, found 414.2189.

8.1.26. Formation and structural analysis of Ethyl (2-(7-ethyl-1-((2-ethylphenyl)amino)-2-oxoindolin-3-yl)acetyl)carbamate (4h)

[Formula 4h]

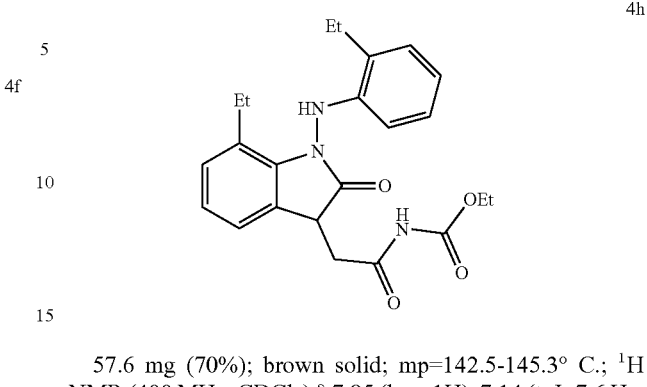

4h 57.6 mg (70%); brown solid; mp=142.5-145.3° C.; $^1$H NMR (400 MHz, CDCl$_3$) δ 7.85 (br s, 1H), 7.14 (t, J=7.6 Hz, 2H), 7.10-7.00 (m, 3H), 6.91-6.88 (m, 1H), 6.67-6.61 (m, 2H), 4.18 (q, J=7.2 Hz, 2H), 3.92 (t, J=5.6 Hz, 1H), 3.55 (dd, J=18.4, 4.4 Hz, 1H), 3.34 (dd, J=18.4, 6.8 Hz, 1H), 2.71-2.66 (m, 4H), 1.32 (t, J=7.6 Hz, 3H), 1.28 (t, J=7.2 Hz, 3H), 1.14 (t, J=7.6 Hz, 3H); $^{13}$C NMR (100 MHz, CDCl$_3$) δ 176.6, 171.3, 151.6, 144.1, 140.1, 130.3, 128.9, 128.5, 127.2, 126.9, 126.5, 123.1, 121.5, 121.4, 112.1, 62.4, 39.5, 36.9, 23.8, 23.4, 16.5, 14.1, 13.3; IR (KBr) υ 3282, 2960, 2924, 2853, 2363, 2339, 1760, 1707, 1607, 1510, 1455, 1410, 1267, 1221, 1172, 1075, 742 cm$^{-1}$; HRMS (orbitrap, ESI) calcd for C$_{23}$H$_{28}$N$_3$O$_4$ [M+H]+ 410.2074, found 410.2091.

8.1.27. Formation and structural analysis of Methyl (2-(7-ethyl-1-((2-ethylphenyl)amino)-2-oxoindolin-3-yl)acetyl)carbamate (4i)

[Formula 4i]

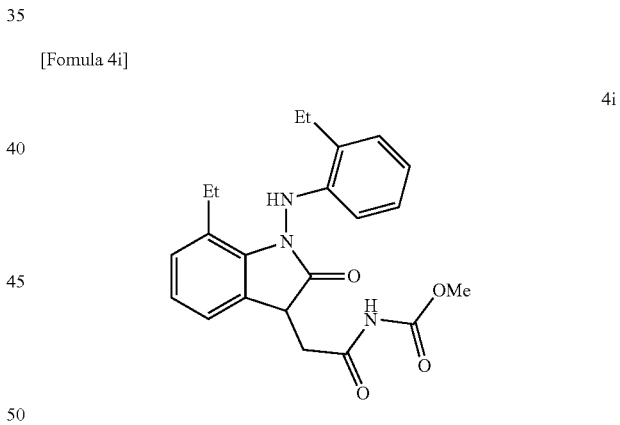

4i 34.8 mg (44%); brown solid; mp=137.6-140.3° C.; $^1$H NMR (400 MHz, CDCl$_3$) δ 8.02 (br s, 1H), 7.14 (t, J=8.0 Hz, 2H), 7.09 (d, J=7.2 Hz, 1H), 7.04-7.00 (m, 2H), 6.89 (t, J=7.6 Hz, 1H), 6.65-6.62 (m, 2H), 3.92 (t, J=5.2 Hz, 1H), 3.75 (s, 3H), 3.55 (dd, J=18.0, 4.0 Hz, 1H), 3.32 (dd, J=18.0, 6.4 Hz, 1H), 2.83-2.65 (m, 4H), 1.32 (t, J=7.6 Hz, 3H), 1.14 (t, J=7.6 Hz, 3H); $^{13}$C NMR (100 MHz, CDCl$_3$) δ 176.8, 171.2, 152.1, 144.1, 140.1, 130.3, 128.9, 128.5, 127.3, 126.9, 126.5, 123.1, 121.5, 121.4, 112.2, 53.1, 39.5, 36.9, 23.7, 23.4, 16.5, 13.3; IR (KBr) υ 3285, 3057, 2957, 2922, 2853, 2360, 1764, 1706, 1606, 1504, 1455, 1379, 1295, 1209, 1077, 963, 748 cm$^{-1}$; HRMS (orbitrap, ESI) calcd for C$_{22}$H$_{26}$N$_3$O$_4$ [M+H]$^+$ 396.1918, found 396.1932.

8.1.28. Formation and structural analysis of Methyl (2-(7-ethyl-1-((2-ethylphenyl)amino)-2-oxoindolin-3-yl)acetyl)-L-alaninate (4j)

[Fomula 4j]

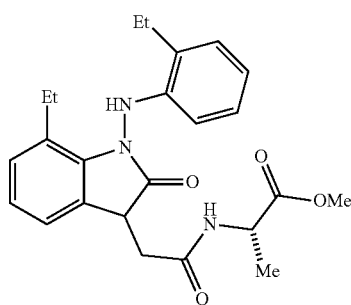

4j 67.1 mg (79%, dr=1:1); brown sticky solid; ¹H NMR (400 MHz, CDCl₃) δ 7.21-7.15 (m, 2H), 7.10-7.02 (m, 3H), 6.90 (td, J=7.6, 3.2 Hz, 1H), 6.64-6.57 (m, 2H), 4.62-4.57 (m, 1H), 3.95 (t, J=6.0 Hz, 1H), 3.72 (d, J=2.0 Hz, 3H), 2.96 (dd, J=15.6, 5.6 Hz, 1H), 2.92-2.66 (m, 5H), 1.40-1.31 (m, 6H), 1.13 (td, J=7.2, 1.6 Hz, 3H); ¹³C NMR (100 MHz, CDCl₃) δ: 176.8, 173.4, 173.3 (diastereomeric), 169.3, 169.2 (diastereomeric), 144.1, 144.0 (diastereomeric), 139.8, 130.5, 130.4 (diastereomeric), 129.0, 128.9 (diastereomeric), 128.7, 127.3, 127.0, 126.9 (diastereomeric), 126.4, 126.2 (diastereomeric), 123.2, 122.1, 121.9 (diastereomeric), 121.7, 121.5 (diastereomeric), 112.0, 111.9 (diastereomeric), 52.5, 52.4 (diastereomeric), 48.2, 48.1 (diastereomeric), 40.7, 40.3 (diastereomeric), 37.0, 36.9 (diastereomeric), 23.8, 23.7 (diastereomeric), 23.5, 23.4 (diastereomeric), 18.3, 18.2 (diastereomeric), 16.5, 16.4 (diastereomeric), 13.4, 13.3 (diastereomeric); IR (KBr) υ 3314, 3059, 2962, 2914, 2871, 1714, 1661, 1606, 1536, 1454, 1375, 1295, 1265, 1212, 1164, 1054, 982, 845, 737 cm⁻¹; HRMS (orbitrap, ESI) calcd for C₂₄H₃₀N₃O₄ [M+H]⁺ 424.2231, found 424.2246.

8.2 synthesis of oxindole derivatives using maleate and fumarate as substrates 8.2.1. Formation and structural analysis of Methyl 2-(7-ethyl-1-((2-ethylphenyl)amino)-2-oxoindolin-3-yl)acetate (6a)

[Fomula 6a]

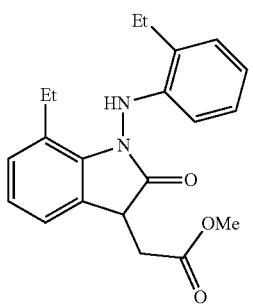

6a 36.1 mg (51%); brown sticky oil; ¹H NMR (400 MHz, CDCl₃) δ 7.18-7.12 (m, 3H), 7.10-7.01 (m, 2H), 6.91 (td, J=7.6, 1.2 Hz, 1H), 6.63 (d, J=8.0 Hz, 1H), 6.54 (s, 1H), 3.87 (br s, 1H), 3.69 (s, 3H), 3.08 (dd, J=16.8, 4.8 Hz, 1H), 2.90 (dd, J=16.8, 7.2 Hz, 1H), 2.74-2.68 (m, 4H), 1.34 (t, J=7.2 Hz, 3H), 1.14 (t, J=7.6 Hz, 3H); ¹³C NMR (100 MHz, CDCl₃) δ 176.0, 171.2, 144.2, 140.1, 130.5, 129.0, 128.7, 127.3, 127.0, 126.2, 123.1, 121.7, 121.5, 112.2, 52.1, 40.1, 34.6, 23.8, 23.4, 16.4, 13.3; IR (KBr) υ 3286, 3059, 2964, 2928, 2872, 2352, 1721, 1605, 1589, 1508, 1481, 1455, 1437, 1368, 1294, 1265, 1211, 1170, 1066, 993, 937, 827, 746 cm⁻¹; HRMS (orbitrap, ESI) calcd for C₂₁H₂₅N₂O₃ [M+H]⁺ 353.1860, found 353.1875.

8.2.2. Formation and structural analysis of Butyl 2-(7-ethyl-1-((2-ethylphenyl)amino)-2-oxoindolin-3-yl)acetate (6b)

[Fomula 6b]

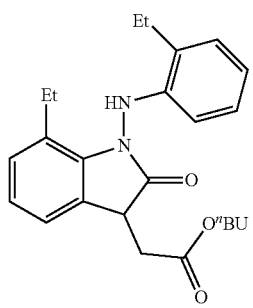

6b 28.7 mg (36%); brown sticky solid; ¹H NMR (400 MHz, CDCl₃) δ 7.29 (d, J=7.2 Hz, 1H), 7.15 (d, J=6.4 Hz, 2H), 7.09-7.04 (m, 2H), 6.91 (t, J=7.6 Hz, 1H), 6.68 (d, J=7.6 Hz, 1H), 6.54 (s, 1H), 4.63 (br s, 1H), 4.08 (t, J=6.8 Hz, 2H), 3.02-2.90 (m, 2H), 2.73-2.64 (m, 4H), 1.57-1.50 (m, 2H), 1.33-1.24 (m, 5H), 1.13 (t, J=7.6 Hz, 3H), 0.87 (t, J=7.2 Hz, 3H); ¹³C NMR (100 MHz, CDCl₃) δ 175.7, 170.4, 143.8, 139.4, 132.3, 128.9, 128.7, 128.1, 127.8, 127.1, 123.8, 121.7, 121.5, 112.0, 71.6, 65.1, 41.1, 30.3, 23.7, 23.5, 18.9, 16.4, 13.6, 13.3; IR (KBr) υ 3289, 3062, 2960, 2927, 2872, 2371, 1731, 1604, 1589, 1508, 1455, 1390, 1320, 1293, 1265, 1184, 1058, 1037, 954, 871, 799, 743 cm⁻¹; HRMS (quadrupole, EI) calcd for C₂₄H₃₀N₂O₃ [M]⁺ 394.2256, found 394.2255.

8.2.3. Formation and structural analysis of Isopropyl 2-(7-ethyl-1-((2-ethylphenyl)amino)-2-oxoindolin-3-yl)acetate (6c)

[Fomula 6c]

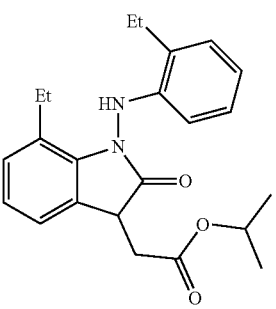

6c 46.6 mg (61%); pale yellow oil; ¹H NMR (400 MHz, CDCl₃) δ 7.16 (t, J=7.6 Hz, 2H), 7.09 (t, J=7.6 Hz, 1H), 7.06-7.01 (m, 2H), 6.91 (td, J=7.2, 0.8 Hz, 1H), 6.63 (d, J=7.6 Hz, 1H), 6.54 (s, 1H), 5.02 (br s, 1H), 3.89-3.86 (m, 1H), 3.05 (dd, J=16.8, 4.4 Hz, 1H), 2.86-2.68 (m, 5H), 1.34 (t, J=7.6 Hz, 3H), 1.22-1.12 (m, 9H); ¹³C NMR (100 MHz, CDCl₃) δ 176.1, 170.3, 144.2, 140.1, 130.4, 129.0, 128.6, 127.2, 126.9, 126.5, 123.1, 121.7, 121.5, 112.2, 68.5, 40.2, 35.2, 23.8, 23.4, 21.8, 21.7, 16.4, 13.3; IR (KBr) υ 3288, 3062, 2965, 2928, 2872, 2368, 1722, 1604, 1507, 1454, 1373, 1319, 1293, 1211, 1195, 1105, 1066, 962, 741 cm$^{-1}$; HRMS (orbitrap, ESI) calcd for $C_{23}H_{29}N_2O_3$ [M+H]$^+$ 381.2173, found 381.2180.

8.2.4. Formation and structural analysis of Isobutyl 2-(7-ethyl-1-((2-ethylphenyl)amino)-2-oxoindolin-3-yl)acetate (6d)

[Fomula 6d]

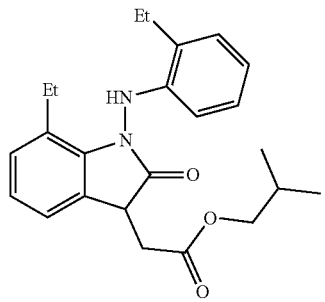

6d 57.7 mg (73%); brown sticky solid; $^1$H NMR (400 MHz, CDCl$_3$) δ 7.18-7.01 (m, 5H), 6.91 (t, J=7.2 Hz, 1H), 6.64 (d, J=7.6 Hz, 1H), 6.57 (s, 1H), 3.89-3.87 (m, 2H), 3.11 (dd, J=16.8, 4.4 Hz, 1H), 2.93-2.68 (m, 5H), 1.93-1.87 (m, 1H), 1.34 (t, J=7.6 Hz, 3H), 1.15 (t, J=7.6 Hz, 3H), 0.89 (d, J=6.8 Hz, 3H); $^{13}$C NMR (100 MHz, CDCl$_3$) δ 176.0, 170.8, 144.2, 140.1, 130.4, 128.9, 128.6, 127.2, 126.9, 126.4, 123.1, 121.6, 121.5, 112.1, 71.1, 40.1, 34.8, 27.6, 23.8, 23.4, 19.0, 16.4, 13.3; IR (KBr) υ 3291, 3061, 2963, 2931, 2873, 2362, 1728, 1604, 1504, 1455, 1378, 1265, 1188, 1159, 1063, 997, 943, 737 cm$^{-1}$; HRMS (orbitrap, ESI) calcd for $C_{24}H_{31}N_2O_3$ [M+H]$^+$ 395.2329, found 395.2256.

8.3. Synthesis of indole using maleate and azobenzene 8.3.1. Formation and structural analysis of Dibutyl 6-ethyl-1H-indole-2,3-dicarboxylate (7a)

[RhCp*Cl$_2$]$_2$ (3.1 mg, 0.005 mmol, 2.5 mol %). AgSbF$_6$ (6.9 mg, 0.02 mmol, 10 mol %) and Cu(OAc)$_2$ (36.3 mg, 0.2 mmol, 100 mol %) were mixed in an oven dried sealed tube charged with (E)-1,2-bis(3-ethylphenyl)diazene (1o) (47.7 mg, 0.2 mmol, 100 mol %). Then, dibutyl maleate (5b) (68.5 mg, 0.3 mmol, 150 mol %) and DCE (0.5 mL) were treated and reacted at room temperature and air. After the reaction mixture was stirred at 130° C. for 12 hours, the reaction mixture was cooled to room temperature, and the reaction mixture was diluted with EtOAc (3 mL) and concentrated in vacuo. The residue was purified by flash column chromatography (n-Hexane/EtOAc=10:1) to give 7a (41.6 mg) in 60% yield.

[Fomula 7a]

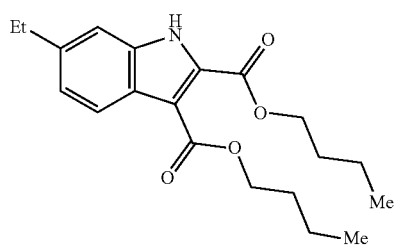

7a 41.6 mg (60%); brown sticky solid; $^1$H NMR (500 MHz, CDCl$_3$) δ 9.10 (br s, 1H), 7.91 (d, J=8.5 Hz, 1H), 7.23 (s, 1H), 7.12 (dd, J=8.5, 1.0 Hz, 1H), 4.40-4.36 (m, 4H), 2.75 (q, J=7.5 Hz, 2H), 1.82-1.73 (m, 4H), 1.63 (s, 1H), 1.52-1.44 (m, 4H), 1.28 (t, J=7.5 Hz, 3H), 1.00-0.95 (m, 6H); $^{13}$C NMR (125 MHz, CDCl$_3$) δ 164.3, 161.1, 142.6, 135.2, 127.5, 125.0, 123.5, 122.3, 112.3, 110.1, 65.6, 64.6, 30.8, 30.6, 29.2, 19.3, 19.1, 15.7, 13.8, 13.7; IR (KBr) υ 3313, 3053, 2958, 2926, 2871, 2359, 1698, 1571, 1535, 1507, 1455, 1428, 1378, 1327, 1264, 1215, 1182, 1135, 1067, 963, 862, 819, 771, 740 cm$^{-1}$; HRMS (quadrupole, EI) calcd for $C_{20}H_{27}NO_4$ [M]$^+$ 345.1940, found 345.1940.

8.4. Synthesis and structure analysis of free-(NH)-oxindoles 8a and 8b

An excess of Raney nickel (150 mg, slurry in H$_2$O) in EtOH (1 mL) solution was added to 2-(7-ethyl-1-((2-ethylphenyl)amino)-2-oxoindolin-3-yl)-N-methylacetamide (3a) (70.3 mg, 0.2 mmol, 100 mol %). The mixture was stirred at 80° C. for 16 hours under H$_2$ atmosphere. The reaction mixture was filtered, washed with dichloromethane (20 mL) and concentrated in vacuo. The residue was purified by flash column chromatography (DCM/MeOH=50:1) to give 5a (23.8 mg) in 51% yield.

8.4.1. Formation and structural analysis of 2-(7-Ethyl-2-oxoindolin-3-yl)-N-methylacetamide (8a)

[Fomula 8a]

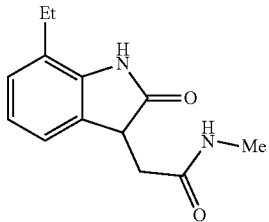

8a 23.8 mg (51%); white solid; mp=222.4-224.6° C.; $^1$H NMR (400 MHz, CDCl$_3$) δ8.36 (s, 1H), 7.11 (d, J=7.2 Hz, 1H), 7.07 (d, J=7.6 Hz, 1H), 6.99 (t, J=7.6 Hz, 1H), 6.46 (br s, 1H), 3.91 (t, J=5.2 Hz, 1H), 2.91-2.85 (m, 4H), 2.63-2.56 (m, 3H), 1.24 (t, J=7.6 Hz, 3H); $^{13}$C NMR (100 MHz, CDCl$_3$) δ180.1, 170.8, 138.9, 128.7, 127.8, 125.1, 122.9, 121.9, 42.9, 37.3, 26.5, 23.9, 13.9; IR (KBr) υ 3185, 2878, 2424, 2361, 1780, 1700, 1632, 1485, 1452, 1404, 1265, 1298, 1158, 982, 745 cm$^{-1}$; HRMS (orbitrap, ESI) calcd for $C_{13}H_{17}N_2O_2$ [M+H]$^+$ 233.1285, found 233.1288.

8.4.2. Formation and Structural Analysis of Isopropyl 2-(7-ethyl-2-oxoindolin-3-yl)acetate (8b)

[Fomula 8b]

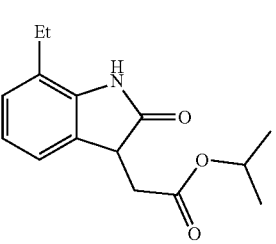

8b 33.5 mg (64%); white solid; mp=84.9-87.2° C.; $^1$H NMR (400 MHz, CDCl$_3$) δ9.35 (s, 1H), 7.07 (d, J=8.4 Hz, 2H), 6.96 (d, J=7.2 Hz, 1H), 5.01-4.96 (m, 1H), 3.85-3.82 (m, 1H), 3.03 (dd, J=16.4, 4.4 Hz, 1H), 2.80 (dd, J=16.8, 8.0 Hz, 1H), 2.63 (q, J=7.6 Hz, 2H), 1.25 (t, J=7.6 Hz, 3H), 1.19 (d, J=6.0 Hz, 3H), 1.11 (d, J=6.0 Hz, 3H); $^{13}$C NMR (100 MHz, CDCl$_3$) δ179.9, 170.4, 139.8, 128.5, 127.7, 125.5, 122.5, 121.5, 68.4, 42.8, 35.2, 23.9, 21.7, 21.5, 14.0; IR (KBr) υ 3189, 3074, 2973, 2926, 2873, 2359, 1707, 1622, 1451, 1412, 1374, 1333, 1265, 1213, 1106, 960, 746 cm$^{-1}$; HRMS (orbitrap, ESI) calcd for C$_{15}$H$_2$NO$_3$ [M+H]$^+$ 262.1438, found 262.1447.

Example 9

Evaluation of Anticancer Activity of Oxindole Derivatives

To evaluate the anticancer activity of the oxindole derivatives produced and analyzed in examples 1 to 8, MTT assay was performed to confirm the growth inhibitory effect on cancer cells. More specifically, human prostate adenocarcinoma cell line (LNCaP), human breast cancer cell line (MCF-7), human ovarian cancer cell line (SKOV3), human lung cancer cell line (A459) and human renal adenocarcinoma cell line (786-O) were cultured in DMEM medium supplemented with 1% penicillin/streptomycin and 10% fetal bovine serum (All from Life Technologies, Grand Island, N.Y.). Cells were seeded in 96-well plates (3×10$^3$ cells/well) containing 100 μL of growth medium for 24 hours. After the medium was removed, 100 μL of each of the different analogues (dissolved in DMSO to 0.025% or less) was added to each well and cultured at 37° C. for 48 hours. After 48 hours of incubation, 100 μL of MTT reagent was added to each well. After incubation at 37° C. for 4 hours, the supernatant was aspirated, and the formazan crystals were dissolved in 100 μL of DMSO at 37° C. for 10 minutes with gentle stirring. Absorbance per well was measured at 540 nm using a VERSA max microplate reader (Molecular Devices Corp.). IC$_{50}$ values were defined as compound concentrations that inhibited cell proliferation by 50% compared to cells treated with the highest amount of DMSO (0.025%) and were considered to be 100% viability.

As a result, as shown in table 3 below, the oxindole derivatives showed excellent anticancer activity as a whole, in particular, 3e, 3f, 4c, 4g, 6b, 6d, and 7a showed excellent inhibitor) activity against all carcinomas. 3i showed excellent inhibitor activity in LNCaP and 786-O, 4b showed excellent activity in LNCaP, A549, and 786-O, and 6c in LNCaP in particular.

These results imply that the oxindole derivatives produced by the method of the present invention can be used as a novel inhibitor for prostate cancer, breast cancer, ovarian cancer, lung cancer and kidney cancer.

TABLE 3

| compound | LNCaP (IC50, μM) | MCF-7 (IC50, μM) | SKOV3 (IC50, μM) | A549 (IC50, μM) | 786-O (IC50, μM) |
| --- | --- | --- | --- | --- | --- |
| 3b | >50 | >50 | >50 | >50 | >50 |
| 3c | 44.6 | >50 | >50 | >50 | 40.9 |
| 3d | >50 | >50 | >50 | >50 | >50 |
| 3e | 15.5 | 20.5 | 21.3 | 33.3 | 14.7 |
| 3f | 12.8 | 14.8 | 16.9 | 24.0 | 13.3 |
| 3g | >50 | >50 | >50 | >50 | >50 |
| 3h | 42.9 | >50 | >50 | >50 | 41.3 |
| 3i | 30.2 | >50 | 44.5 | >50 | 29.5 |
| 3k | >50 | >50 | >50 | >50 | >50 |
| 3l | 42.4 | >50 | >50 | >50 | 42.67 |
| 3m | >50 | >50 | >50 | >50 | >50 |
| 3n | >50 | >50 | >50 | >50 | >50 |
| 3o | >50 | >50 | >50 | >50 | >50 |
| 4b | 32.2 | >50 | >50 | >50 | >50 |
| 4c | 12.2 | 16.6 | 20.3 | 28.9 | 10.5 |
| 4d | 33 | 40.4 | >50 | >38.6 | 33.1 |
| 4e | 15.3 | >50 | >50 | >50 | 36.6 |
| 4f | >50 | >50 | >50 | >50 | >50 |
| 4g | 6 | 9.6 | 13.8 | 16.8 | 4.8 |
| 4h | >50 | >50 | >50 | >50 | >50 |
| 4i | 33.5 | >50 | >50 | >50 | 32.6 |
| 4j | >50 | >50 | >50 | >50 | >50 |
| 6a | >50 | >50 | >50 | >50 | >50 |
| 6b | 13.9 | 14.7 | 15.1 | 17.6 | 12.2 |
| 6c | 14.5 | 45.5 | >50 | >50 | 30.5 |
| 6d | 12.5 | 14.2 | 14.5 | 22.5 | 12.6 |
| 7a | 14.5 | 20.6 | 22.1 | 24.4 | 13.2 |
| 8b | >50 | >50 | >50 | >50 | >50 |

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are only illustrative in all aspects and are not restrictive.

The invention claimed is:

1. An oxindole derivative represented by following Formula 1, an isomer thereof, or a pharmaceutically acceptable salt thereof:

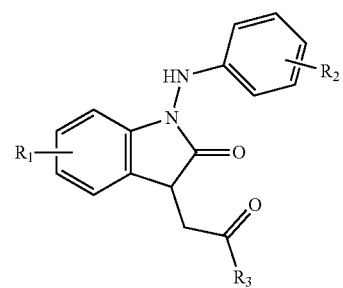

[Formula 1]

in the Formula 1,
wherein R$_1$ and R$_2$ are one or more substituents and are independently hydrogen, halogen, or C1-C6 alkyl, and each of R$_1$ and R$_2$ is a substituent at least at an ortho, meta or para position;
wherein R$_3$ is NHMe, NHEt, NHBn, NHCyHex, NH$^t$Bu, NH$_2$, NHPh, NHCH$_2$Ph, NHCO$_2$Me, NHCO$_2$Et, NHCHCH$_3$CO$_2$Me, OMe, O$^n$Bu, O$^i$Pr, or O$^i$Bu;
wherein Me is CH$_3$, Et is CH$_2$CH$_3$, Bn is CH$_2$Ph (benzyl), Cyhex is cyclohexyl, $^t$Bu is tertiarybutyl, $^n$Bu is nor-malbutyl, $^i$Pr is iso Isopropyl, and $^i$Bu is isobutyl.

2. An oxindole derivative, an isomer thereof, or a pharmaceutically acceptable salt thereof of claim 1, selected from the group consisting of:

2-(7-Ethyl-1-((2-ethylphenyl)amino)-2-oxoindolin-3yl)-
  N-methylacetamide (3a);
N-methyl-2-(7-methyl-2-oxo-1-(o-tolylamino)indolin-3-
  yl)acetamide (3b);
2-(1-((2,3-dimethyrlphenyl)amino)-6,7-dimethyl-2-ox-
  oindolin-3-yl)-N-methylacetamide (3c);
2-(6-fluoro-1-((3-fluoro-2-methylphenyl)amino)-7-
  methyl-2-oxoindolin-3-yl)-N-methylacetamide (3d);
2-(6-Chloro-1((3-chloro-2-methylphenyl)amino-7-
  methyl-2-oxoindolin-3-yl)-N-methylacetamide (3e);
2-(6-bromo-1-bromo-2-methylphenyl)amino-7-methyl-2-
  oxoindolin-3-yl)-N-methylacetamide (3f);
2-(1((2,4-dimethylphenyl)amino)-5,7-dimethyl-2-oxoin-
  dolin-3-yl)-N-methylacetamide (3g);
2-(5-fluoro-1-((4-fluoro-2-methylphenyl)amino)-7-
  methyl-2-oxoindolin-3-yl)-N-methylacetamide (3h);
2-(5-chloro-1-((4chloro-2-methylphenyl)amino)-7-
  methyl-2-oxoindolin-3-yl-N-methylacetamide (3i);
2-((2,5-dimethylphenyl)amino)-4,7-dimethyl-2-oxoindo-
  lin-3-yl)-N-methylacetamide (3j);
2-(4-fluoro-1-((5-fluoro-2-methylphenyl)amino)-7-
  methyl-2-oxoindolin-3-yl)-N -methylacetamide (3k);
2(4-Bromo-1-(5-bromo-2- methylphenyl) amino)-7-
  methyl-2-oxoindolin-3-yl)-N-methylacetamide (3l);
N-methyl-2-(2-oxo-1-(phenylamino)indolin-3-yl)acet-
  amide (3m);
N-methyl-2-(5-methyl-2-oxo-1-tolylamino)indolin-3-yl)
  acetamide (3n);
2-(6-ethyl-1((3-ethylphenyl)amino)-2-moindolin-3-yl)-
  N-methylacetamide (3o);
2-(1-(2,4-Dimethylphenylamino)-7-methyl-2-oxoindo-
  lin-3-yl)-N-methylacetamide (3p);
2-(5,7-dimethyl-2-oxo-1-(o-tolylamino)indolin-3-yl)-N-
  methylacetamide (3p');
N-methyl-2-(2-oxo-1-(p-tolylamino)indolin-3-yl) acet-
  amide (3q);
N-methyl-2-(5-methyl-2-oxo-1-(phenylamino)indolin-3-
  yl)acetamide (3q ');
2-(1-(4-Chloro-2-methylphenylamino)-7-methyl-2-ox-
  oindolin-3-yl)-N-methylacetamide (3r);
2-(5-chloro-7-methyl-2-oxo-1-(o-tolylamino)indolin-3-
  yl)-N-methylacetamide (3r');
N-Ethyl-2-(7-ethyl-1-((2-ethylphenyl) amino)-2-oxoin-
  dolin-3-yl)acetamide (4b);
N-benzyl-2-(7-ethyl-1-((2-ethylphenyl)amino)-2-oxoin-
  dolin-3-yl)acetamide (4c);
N-cyclohexyl-2-(7-ethyl-1-((2-ethylphenyl)amino)-2-ox-
  oindolin-3-yl)acetamide (4d);
N-(tert-butyl)-2-(7-ethyl-1((2-ethylphenyl)amino)-2-ox-
  oindolin-3-yl)acetamide (4e);
2-(7-Ethyl-1-((2-ethylphenyl)amino)-2-oxoindolin-3-yl)
  acetamide (4f);
2-(7-Ethyl-1-((2-ethylphenyl)amino)-2-oxoindolin-3-yl)-
  N-phenylacetamide (4g);
Ethyl(2-(7-ethyl-1-((2-ethylphenyl)amino)-2-oxoindolin-
  3-yl)acetyl) carbamate (4h);
Methyl(2-(7-ethyl-1-((2-ethylphenyl)amino)-2-oxoindo-
  lin-3-yl)acetyl)carbamate (4i);
Methyl (2-(7-ethyl-1-((2-ethylphenyl)amino)-2-oxoindo-
  lin-3-yl)acetyl)-L-alaninate (4j);
Methyl 2-(7-ethyl-1-((2-ethylphenyl)amino)-2-oxoindo-
  lin-3-yl)acetate (6a);
Butyl 2-(7-ethyl-1-((2-ethylphenyl) amino)-2-oxoindolin-
  3-yl)acetate (6b);
Isopropyl 2-(7-ethyl-1-((2-ethylphenyl)amino)-2-oxoin-
  dolin-3-yl)acetate (6c); and
Isobutyl 2-(7-ethyl-1-((2-ethylphenyl)amino)-2-oxoindo-
  lin-3-yl)acetate (6d).

3. A preparation method of an oxindole derivative represented by following Formula 1, comprising
  a step (S1) of performing a C-H alkylation reaction in the presence of a rhodium catalyst by mixing a compound represented by following Formula 2, a compound represented by following Formula 3 or 4, and an additive; and
  a step (S2) of performing an intramolecular cyclization reaction by adding a zinc powder and an additive after the C—H alkylation reaction:

[Formula 1]

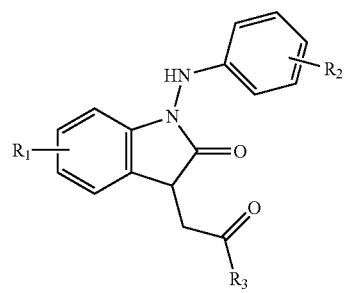

[Formula 2]

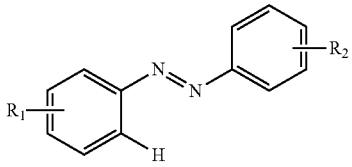

[Formula 3]

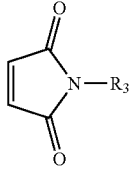

[Formula 4]

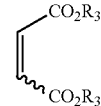

in the Formulas 1 to 4,
  wherein $R_1$ and $R_2$ are one or more substituents and are independently hydrogen, halogen, or C1-C6 alkyl, and each of $R_1$ and $R_2$ is a substituent at least at an ortho, meta or para position;
  wherein $R_3$ is NHMe, NHEt, NHBn, NHCyHex, NH$^t$Bu, NH$_2$, NHPh, NHCH$_2$Ph, NHCO$_2$Me, NHCO$_2$Et, NHCHCH$_3$CO$_2$Me, OMe, O"Bu, O$^i$Pr, or O$^i$Bu;
  wherein Me is CH$_3$, Et is CH$_2$CH$_3$, Bn is CH$_2$Ph (benzyl), Cyhex is cyclohexyl, $^t$Bu is tertiarybutyl, "Bu is normalbutyl, $^i$Pr is iso Isopropyl, and $^i$Bu is isobutyl.

4. The method of claim 3, wherein the rhodium catalyst is a cyclopentadienyl rhodium (III) complex catalyst substituted or unsubstituted with a C1-C5 alkyl.

5. The method of claim 4, wherein the rhodium catalyst is a. pentamethylcyclopentadienylrhodium (III) chloride dimer catalyst.

6. The method of claim 3, wherein the additive in step (S2) is an acid additive.

7. The method of claim 6, wherein the acid additive in step (S2) is acetic acid, ammonium chloride (NH$_4$Cl) or a mixture thereof.

8. The method of claim 3, wherein the step (S1) is performed in a dichloroethene (DCE) solvent.

9. The method of claim 3, wherein the step (S2) is performed in a solvent of ethanol, methanol or a mixture thereof.

10. The method of claim 3, wherein the additive in the step (S1) is an acid additive.

11. The method of claim 10, wherein the acid additive in step (S1) is pivalic acid, acetic acid, or a mixture thereof.

12. A method for treating cancer, which comprises administering an oxindole derivative, an isomer thereof, or a pharmaceutically acceptable salt thereof of claim 1 to a cancer patient for treatment of cancer.

13. The method of claim 12, wherein the cancer is selected from the group consisting of prostate cancer, breast cancer, ovarian cancer, lung cancer, and kidney cancer.

* * * * *